United States Patent
Kawasaki et al.

(10) Patent No.: US 9,234,845 B2
(45) Date of Patent: Jan. 12, 2016

(54) MICROSCOPE WITH REFLECTING FLUORESCENCE ILLUMINATION OPTICAL SYSTEM

(75) Inventors: Kenji Kawasaki, Hachioji (JP); Yoshihiro Shimada, Sagamihara (JP)

(73) Assignee: OLYMPUS CORPORATION, Tokyo (JP)

(*) Notice: Subject to any disclaimer, the term of this patent is extended or adjusted under 35 U.S.C. 154(b) by 248 days.

(21) Appl. No.: 12/090,763

(22) PCT Filed: Oct. 19, 2007

(86) PCT No.: PCT/JP2007/070405
§ 371 (c)(1),
(2), (4) Date: Apr. 18, 2008

(87) PCT Pub. No.: WO2008/047893
PCT Pub. Date: Apr. 24, 2008

(65) Prior Publication Data
US 2009/0195866 A1 Aug. 6, 2009

(30) Foreign Application Priority Data
Oct. 19, 2006 (JP) .................................. 2006285054

(51) Int. Cl.
*G02B 21/06* (2006.01)
*G01N 21/64* (2006.01)
(Continued)

(52) U.S. Cl.
CPC ........ *G01N 21/6458* (2013.01); *G02B 13/0095* (2013.01); *G02B 21/16* (2013.01); *G02B 21/0032* (2013.01); *G02B 21/0076* (2013.01); *G02B 21/367* (2013.01)

(58) Field of Classification Search
CPC .... G02B 21/06; G02B 21/0076; G02B 21/16; G02B 21/0032; G02B 21/367; G02B 13/0095

USPC ......... 359/368–398; 250/458.1, 459.1, 461.1, 250/461.2
See application file for complete search history.

(56) References Cited

U.S. PATENT DOCUMENTS 4,062,619 A * 12/1977 Hoffman ........................ 359/370
4,407,569 A * 10/1983 Piller et al. .................... 359/370
(Continued)

FOREIGN PATENT DOCUMENTS

| EP | 0 069 263 | 1/1983 |
| JP | 10221607 | 8/1998 |

(Continued)

OTHER PUBLICATIONS

International Search Report, dated Jan. 22, 2008, in corresponding PCT application, 4 pp.
(Continued)

*Primary Examiner* — Stephone B Allen
*Assistant Examiner* — Tamara Y Washington
(74) *Attorney, Agent, or Firm* — Pillsbury Winthrop Shaw Pittman, LLP

(57) ABSTRACT

A microscope includes an objective lens, an imaging lens projecting light passing through the objective lens to form an image of a specimen, an image sensor located at an imaging position where the image of the specimen is formed, an illumination light source, and a reflecting fluorescence illumination optical system including a dichroic mirror introducing light from the illumination light source into an optical to illuminate the specimen with the light. The microscope further includes a relay optical system forming an intermediate image of the specimen between the objective lens and the imaging lens to relay it to the imaging lens. The dichroic mirror of the reflecting fluorescence illumination optical system is located between the relay optical system and a pupil conjugate position that is conjugate with a pupil position of the objective lens, formed between the relay optical system and the imaging lens.

44 Claims, 19 Drawing Sheets

(51) Int. Cl.
*G02B 13/00* (2006.01)
*G02B 21/16* (2006.01)
*G02B 21/00* (2006.01)
*G02B 21/36* (2006.01)

(56) References Cited

U.S. PATENT DOCUMENTS

| | | | |
|---|---|---|---|
| 5,729,385 A | 3/1998 | Nishida et al. | |
| 6,028,306 A * | 2/2000 | Hayashi | 250/235 |
| 6,404,545 B1 * | 6/2002 | Ishiwata | 359/371 |
| 6,741,394 B1 * | 5/2004 | Tanitsu et al. | 359/619 |
| 6,940,640 B2 * | 9/2005 | Sukekawa et al. | 359/368 |
| 6,940,641 B2 * | 9/2005 | Abe | 359/385 |
| 2004/0120034 A1 * | 6/2004 | Miyawaki et al. | 359/385 |
| 2005/0068614 A1 * | 3/2005 | Yoneyama et al. | 359/368 |
| 2006/0061857 A1 * | 3/2006 | Lee et al. | 359/368 |
| 2006/0114554 A1 | 6/2006 | Suzuki et al. | |

FOREIGN PATENT DOCUMENTS

| | | |
|---|---|---|
| JP | 2000-098244 | 4/2000 |
| JP | 2002040327 | 2/2002 |
| JP | 2003005083 | 1/2003 |
| JP | 2004212469 | 7/2004 |
| JP | 2005517217 A1 | 6/2005 |
| JP | 2006119645 | 5/2006 |
| JP | 2006189616 | 7/2006 |
| JP | 2006220994 | 8/2006 |
| WO | 03067632 | 8/2003 |

OTHER PUBLICATIONS

European Search Report dated Jul. 28, 2010.

* cited by examiner

MICROSCOPE WITH REFLECTING FLUORESCENCE ILLUMINATION OPTICAL SYSTEM

This is the U.S. National Stage of International Application No. PCT/JP2007/070405, filed on Oct. 19, 2007, which, in turn, relies for priority upon Japanese Patent Application No. 2006-285054, filed on Oct. 19, 2006, the contents of both of which are hereby incorporated by reference in their entireties.

TECHNICAL FIELD

This invention relates to a microscope in which an image of a specimen is formed and observed.

BACKGROUND ART

FIG. 1 is a conceptual view showing an example of a fundamental optical arrangement of a conventional microscope of this type. Also, for convenience of comparison with the present invention to be described later, the figure is upside down.

The microscope shown in FIG. 1 has an objective lens 51, an imaging lens 52, an image sensor 53, an illumination light source 54, and a reflecting fluorescence illumination optical system 56. Also, in FIG. 1, reference symbol P denotes the pupil position of the objective lens 51 and O denotes the center axis of the objective lens 51 and the imaging lens 52. The imaging lens 52 is designed to project light passing through the objective lens 51 and to form the image of a specimen 57.

The image sensor 53 is located at the position where the image of the specimen 57 is formed by the imaging lens 52. The reflecting fluorescence illumination optical system 56 is constructed to have a dichroic mirror 55 introducing light from the illumination light source 54 into an optical path on the objective-lens-51 side and to illuminate the specimen 57 with the light.

In the microscope shown in FIG. 1, a desired optical member is inserted in the optical path between the objective lens 51 and the imaging lend 52 in accordance with an observation application. In the example of FIG. 1, an arrangement for a fluorescence observation is shown, and an excitation filter 58 and a barrier filter 59 are arranged on the illumination-light-source-54 side of the dichroic mirror 55 and on the specimen-57 side, respectively.

In the microscope shown in FIG. 1, light emitted from the illumination light source 54 is incident on the reflecting fluorescence illumination optical system 56, and light with excitation wavelength alone is extracted through the excitation filter 58 in the reflecting fluorescence illumination optical system 56 and is incident on the dichroic mirror 55. The light is reflected by the dichroic mirror 55 and enters the objective lens 51 to irradiate the specimen 57 through the objective lens 51. Light from the specimen 57, containing fluorescent light, passes through the objective lens 51 and is transmitted through the dichroic mirror 55 to enter the barrier filter 59. Light in which unwanted wavelength other than desired fluorescent light is cut off through the barrier filter 59 is incident on the imaging lens 52 and is formed as the image of the specimen 57 on the image pickup surface of the image sensor 53 through the imaging lens 52 so that the image is picked up by the image sensor 53. The image of the specimen 57 picked up by the image sensor 53 can be observed as a picture through a display device omitted from the figure. A conventional microscope of such a type is set forth, for example, in Japanese Patent Kokai No. 2000-98244.

DISCLOSURE OF THE INVENTION

In the conventional microscope of the type such as that shown in FIG. 1, rays of light which travel through optical paths deviating from the center axis O (off-axis rays) are bent by preset angles through the objective lens 51 so that light beams are incident on the imaging lens 52 in a nearly parallel state. In such an arrangement, if an optical path length between the objective lens 51 and the imaging lens 52 is increased, a light beam traveling through the periphery will be away from a light bean traveling through the center in going from the objective lens 51 to the imaging lens 52. As a result, the light traveling through the periphery is eclipsed and ceases to be incident on the barrier filter 59 and the imaging lens 52, and the amount of light imaged on the periphery of the image pickup surface of the image sensor 53 becomes smaller than that at the center.

In recent microscopes, however, there is a tendency that an observation unit is inserted in the optical path and the optical path between the objective lens 51 and the imaging lens 52 is elongated so that the microscopes are capable of accommodating various observation applications. Hence, the periphery of the image obtained by an insufficient amount of marginal light on the image pickup surface is liable to become dark.

In the fields of biology and medicine, however, when a lesion part is diagnosed with colors of cells imaged by carrying out the fluorescence observation under the microscope or when a time-lapse observation is made, the fact that the amount of marginal light is insufficient causes difficulties to correct recognition of the possibility of lesion relative to cells captured on the periphery and of a state of a diagnostic object moving within an observation region.

In order to solve the problem of the insufficiency of the amount of marginal light caused by the elongation of the optical path between the objective lens 51 and the imaging lens 52, it is conceivable that a large-diameter imaging lens is used. However, this causes a raise in cost and oversizing of the microscope, and thus is unfavorable for an observation space and observation operation.

Even though the large-diameter imaging lens is used, the barrier filter and the image sensor, for example, used for the fluorescence observation are standardized to preset sizes. Consequently, when the large-diameter imaging lens is used, unwanted light of part of light traveling through the periphery is not cut off by the barrier filter 59 and reaches the image sensor to degrade the accuracy of a fluorescence observation image. In order to form an image in a standardized image pickup area from the large-diameter imaging lens, an angle of incidence of a marginal ray incident on an image pickup surface must be increased, but this increases the influence of shading inherent in the image sensor.

In the conventional microscope constructed as shown in FIG. 1, the dichroic mirror 55 is located at a distance away from the pupil position P of the objective lens 51 and a pupil position conjugate with the pupil position P, and hence a marginal beam passing through the dichroic mirror 55 considerably deviates from a central beam.

In the microscope of this type, when the fluorescence observation is made, a cube provided with the excitation filter 58 and the barrier filter 59 in the proximity of the dichroic mirror 55 is often used, as a unit, to be movable in and out of the optical path. However, for example, when the marginal beam incident on the excitation filter 58 extremely deviates from the central beam, a part of the marginal beam misses the excitation filter 58, and as a result, the brightness and wavelength of light irradiating the surface of the specimen 57 through the objective lens 51 become uneven with respect to the center and periphery on an irradiated surface. Thus, part of the light emitted from the illumination light source 54 and directed toward the excitation filter 58 must be restricted by a stop so that the marginal beam incident on the excitation filter 58 does not extremely deviate from the central beam in the reflecting fluorescence illumination optical system 56. Consequently, the efficiency of utilization of the amount of light from the illumination light source 54 is has been impaired.

In the microscope of this type, it is desired that the optical system is designed so that, in addition to the unit mentioned above, for example, various optical members, such as pupil modulation means, can be located to be movable to and out of preset positions in the optical path according to the observation application. As mentioned above, however, in the optical arrangement of the conventional microscope, the dichroic mirror 55 is located at a distance away from the pupil position P of the objective lens 51 and the conjugate pupil position. Hence, for example, each of the pupil modulation means, such as a variable stop, a phase plate, and a Nomarski prism, cannot be placed in the proximity of the dichroic mirror 55. Moreover, the objective lens must be exchanged with an objective lens having the pupil position according to each of the pupil modulation means. This leads to the complication of operation.

It is, therefore, an object of the present invention to provide a microscope in which the amount of light for forming an image in the image pickup area and the amount of light for illumination in the observation region can be equalized and the amount of light is efficiently utilized to be switchable to various observations.

In order to achieve the above object, the microscope according to the present invention has an objective lens, an imaging lens projecting light passing through the objective lens to form an image of a specimen, an image sensor located at an imaging position where the image of the specimen is formed by the imaging lens, an illumination light source, and a reflecting fluorescence illumination optical system including a dichroic mirror introducing light from the illumination light source into an optical path on the objective lens side, illuminating the specimen with the light. In this case, the microscope further has a relay optical system in which an intermediate image of the specimen is formed between the objective lens and the imaging lens and is relayed to the imaging lens, and the dichroic mirror of the reflecting fluorescence illumination optical system is located between a pupil position conjugate with a pupil position of the objective lens, formed between the relay optical system and the imaging lens, and the relay optical system.

In the microscope of the present invention, it is desirable that the dichroic mirror of the reflecting fluorescence illumination optical system is located on the proximity of the pupil position conjugate with the pupil position of the objective lens, formed between the relay optical system and the imaging lens.

In the microscope of the present invention, it is desirable that a light beam from the specimen is nearly afocal at the pupil position conjugate with the pupil position of the objective lens, formed between the relay optical system and the imaging lens.

In the microscope of the present invention, it is desirable that the imaging lens is constructed with an imaging optical system provided with a zoom optical system or a variable magnification optical system whose magnification is changed stepwise.

In the microscope of the present invention, it is desirable to satisfy the following condition:

$$0.6 \leq |\beta| \leq 1.5$$

where $\beta$ is a pupil relay magnification of the relay optical system from a pupil of the objective lens to a pupil conjugate position.

In the microscope of the present invention, it is desirable to satisfy the following equation:

$$\beta \approx -1$$

where $\beta$ is a pupil relay magnification of the relay optical system.

In the microscope of the present invention, it is desirable that a fly-eye lens is placed in the proximity of a pupil position in the reflecting fluorescence illumination optical system, conjugate with the pupil position of the objective lens.

In the microscope of the present invention, it is desirable that the illumination light source is constructed with a reflector light source, an LED light source, or a fiber light source.

In the microscope of the present invention, it is desirable to have an integrator rod in the reflecting fluorescence illumination optical system.

In the microscope of the present invention, it is desirable that the illumination light source is constructed with the reflector light source; the reflecting fluorescence illumination optical system has a beam conversion optical system carrying out a preset conversion with respect to a light beam emitted from the reflector light source to make a parallel beam emerge therefrom and the fly-eye lens; and the fly-eye lens includes a lens array whose entrance end faces are provided with a plurality of convex surfaces and a lens array whose exit end faces are provided with a plurality of convex surfaces, integrally or separately constructed, so that the parallel beam emerging from the beam conversion optical system is split into a plurality of beams and a plurality of light source images of the reflector light source are formed in the proximity of the exit end faces.

In the microscope of the present invention, it is desirable that the reflector light source is constructed so that a convergent beam is emitted to perform a primary formation of a light source image, and the beam conversion optical system is constructed with a collector lens converting a light beam diverging from the position of the primary formation into a parallel beam.

In the microscope of the present invention, it is desirable that the reflector light source is constructed so that a parallel beam is emitted and the beam conversion optical system is constructed with an afocal system converting the diameter of the parallel beam emitted from the reflector light source so as to become nearly equal to the diameter of the fly-eye lens.

In the microscope of the present invention, it is desirable that the afocal system is constructed so that the parallel beam emitted from the reflector light source is condensed and after the primary formation of the light source image of the reflector light source is performed inside the system, a condensed beam is converted into a parallel beam to emerge therefrom.

In the microscope of the present invention, it is desirable that the illumination light source has a reflector light source emitting a convergent beam to perform a primary formation of a light source image and a fiber having an entrance end face at a position of the primary formation; the reflecting fluorescence illumination optical system has a collector lens converting a divergent beam emerging from an exit end face of the fiber into a parallel beam and the fly-eye lens; and the fly-eye lens has a lens array whose entrance end faces are provided with a plurality of convex surfaces and a lens array whose exit end faces are provided with a plurality of convex surfaces, integrally or separately constructed, so that the parallel beam emerging from the collector lens is split into a plurality of beams and a plurality of light source images of the illumination light source are formed in the proximity of the exit end faces.

In the microscope of the present invention, it is desirable that the illumination light source has a reflector light source emitting a parallel beam, a lens condensing the parallel beam emitted from the reflector light source to perform a primary formation of a light source image of the reflector light source, and a fiber having an entrance end face at a position of the primary formation; the reflecting fluorescence illumination optical system has a collector lens converting a divergent beam emerging from an exit end face of the fiber into a parallel beam and the fly-eye lens; and the fly-eye lens has a lens array whose entrance end faces are provided with a plurality of convex surfaces and a lens array whose exit end faces are provided with a plurality of convex surfaces, integrally or separately constructed, so that the parallel beam emerging from the collector lens is split into a plurality of beams and a plurality of light source images of the illumination light source are formed in the proximity of the exit end faces.

In the microscope of the present invention, it is desirable that the illumination light source has a reflector light source emitting a convergent beam to perform a primary formation of a light source image and an integrator rod having an entrance end face at a position of the primary formation; the reflecting fluorescence illumination optical system has a collector lens converting a divergent beam emerging from an exit end face of the integrator rod into a parallel beam and the fly-eye lens; and the fly-eye lens includes a lens array whose entrance end faces are provided with a plurality of convex surfaces and a lens array whose exit end faces are provided with a plurality of convex surfaces, integrally or separately constructed, so that the parallel beam emerging from the collector lens is split into a plurality of beams and a plurality of light source images of the illumination light source are formed in the proximity of the exit end faces.

In the microscope of the present invention, it is desirable that the illumination light source has a reflector light source emitting a parallel beam, a lens condensing the parallel beam emitted from the reflector light source to perform a primary formation of a light source image of the reflector light source, and an integrator rod having an entrance end face at a position of the primary formation; the reflecting fluorescence illumination optical system has a collector lens converting a divergent beam emerging from an exit end face of the integrator rod into a parallel beam and the fly-eye lens; and the fly-eye lens has a lens array whose entrance end faces are provided with a plurality of convex surfaces and a lens array whose exit end faces are provided with a plurality of convex surfaces, integrally or separately constructed, so that the parallel beam emerging from the collector lens is split into a plurality of beams and a plurality of light source images of the illumination light source are formed in the proximity of the exit end faces.

In the microscope of the present invention, it is desirable that the illumination light source is constructed with an LED light source; the reflecting fluorescence illumination optical system has a collector lens converting a divergent beam emitted from the LED light source into a parallel beam, which is made to emerge, and the fly-eye lens; and the fly-eye lens has a lens array whose entrance end faces are provided with a plurality of convex surfaces and a lens array whose exit end faces are provided with a plurality of convex surfaces, integrally or separately constructed, so that the parallel beam emerging from the collector lens is split into a plurality of beams and a plurality of light source images of the LED light source are formed in the proximity of the exit end faces.

In the microscope of the present invention, it is desirable that the illumination light source has a plurality of LED light sources of different wavelengths, a plurality of first collector lenses provided opposite to the plurality of LED light sources, converting divergent beams emitted from the LED light sources into parallel beams, path combining means combining optical paths of the parallel beams emerging from the first collector lenses, a light-condensing optical system condensing a parallel beam combined through the path combining means to perform a primary formation of a light source image of each of the LED light sources, and a fiber having an entrance end face at a position of the primary formation; the reflecting fluorescence illumination optical system has a second collector lens converting a divergent beam emerging from an exit end face of the fiber into a parallel beam, which is made to emerge, and the fly-eye lens; and the fly-eye lens has a lens array whose entrance end faces are provided with a plurality of convex surfaces and a lens array whose exit end faces are provided with a plurality of convex surfaces, integrally or separately constructed, so that the parallel beam emerging from the second collector lens is split into a plurality of beams and a plurality of light source images of the illumination light source are formed in the proximity of the exit end faces.

In the microscope of the present invention, it is desirable that it is desirable that the illumination light source has a plurality of LED light sources of different wavelengths, a reflector light source emitting a convergent beam to perform a primary formation of a light source image, and a fiber having an entrance end face at a position of the primary formation of the light source image of the reflector light source; the reflecting fluorescence illumination optical system has a plurality of LED emitted-beam conversion collector lenses provided opposite to the plurality of LED light sources, converting divergent beams emitted from the LED light sources into parallel beams, which are made to emerge, a path combining means combining optical paths of the parallel beams emerging from the LED emitted-beam conversion collector lenses, a fiber emergent-beam conversion collector lens converting a divergent beam emerging from an exit end face of the fiber into a parallel beam, which is made to emerge, a mirror placed to be movable in and out of an optical path of the path combining means, making the parallel beam emerging from the fiber emergent-beam conversion collector lens incident on the fly-eye lens when the mirror is inserted in the optical path, and the fly-eye lens; and the fly-eye lens has a lens array whose entrance end faces are provided with a plurality of convex surfaces and a lens array whose exit end faces are provided with a plurality of convex surfaces, integrally or separately constructed, so that the parallel beam emerging from each of the LED emitted-beam conversion collector lenses or from the fiber emergent-beam conversion collector lens is split into a plurality of beams and a plurality of light source images of the illumination light source are formed in the proximity of the exit end faces.

In the microscope of the present invention, it is desirable that the illumination light source has a plurality of LED light sources of different wavelengths, a reflector light source emitting a parallel beam, a lens condensing the parallel beam emitted from the reflector light source to perform a primary formation of a light source image of the reflector light source, and a fiber having an entrance end face at a position of the primary formation of the light source image of the reflector light source; the reflecting fluorescence illumination optical system has a plurality of LED emitted-beam conversion collector lenses provided opposite to the plurality of LED light sources, converting divergent beams emitted from the LED light sources into parallel beams, which are made to emerge, a path combining means combining optical paths of the parallel beams emerging from the LED emitted-beam conversion collector lenses, a fiber emergent-beam conversion collector lens converting a divergent beam emerging from an exit end face of the fiber into a parallel beam, which is made to emerge, a mirror placed to be movable in and out of an optical path of the path combining means, making the parallel beam emerging from the fiber emergent-beam conversion collector lens incident on the fly-eye lens when the mirror is inserted in the optical path, and the fly-eye lens; and the fly-eye lens has a lens array whose entrance end faces are provided with a plurality of convex surfaces and a lens array whose exit end faces are provided with a plurality of convex surfaces, integrally or separately constructed, so that the parallel beam emerging from each of the LED emitted-beam conversion collector lenses or from the fiber emergent-beam conversion collector lens is split into a plurality of beams and a plurality of light source images of the illumination light source are formed in the proximity of the exit end faces.

In the microscope of the present invention, it is desirable that the illumination light source has a reflector light source emitting a convergent beam to perform a primary formation of a light source image and an integrator rod having an entrance end face at a position of the primary formation of the light source image of the reflector light source, and the reflecting fluorescence illumination optical system has a collector lens converting a divergent beam emerging from an exit end face of the integrator rod into a parallel beam.

In the microscope of the present invention, it is desirable that the illumination light source has a reflector light source emitting a parallel beam, a lens condensing the parallel beam emitted from the reflector light source to perform a primary formation of a light source image of the reflector light source, and an integrator rod having an entrance end face at a position of the primary formation, and the reflecting fluorescence illumination optical system has a collector lens converting a divergent beam emerging from an exit end face of the integrator rod into a parallel beam.

In the microscope of the present invention, it is desirable that the illumination light source has an LED light source, a lens condensing a divergent beam emitted from the LED light source to perform a primary formation of a light source image of the LED light source, and an integrator rod having an entrance end face at a position of the primary formation, and the reflecting fluorescence illumination optical system has a collector lens converting a divergent beam emerging from an exit end face of the integrator rod into a parallel beam.

In the microscope of the present invention, it is desirable that the objective lens, the imaging lens, and the relay optical system are constructed to be nearly telecentric optical systems on the surface of an object, at the position of the intermediate image, and on the surface of the image sensor, respectively.

In the microscope of the present invention, it is desirable that, in the reflecting fluorescence illumination optical system, an excitation filter is provided and a barrier filter cutting off unwanted light, of light from the specimen, is placed in the proximity of a pupil position conjugate with the pupil position of the objective lens, formed between the relay optical system and the imaging lens.

In the microscope of the present invention, it is desirable that a pupil modulation means is placed in the proximity of a pupil position conjugate with the pupil position of the objective lens, formed between the relay optical system and the imaging lens.

In the microscope of the present invention, it is desirable that the pupil modulation means is a variable stop.

In the microscope of the present invention, it is desirable that the pupil modulation means is constructed with a member in which a phase film is zonally provided, and a transmitting illumination means is provided to irradiate zonal illumination light corresponding to the member in which the phase film is zonally provided.

In the microscope of the present invention, it is desirable that the pupil modulation means is a Nomarski prism.

In the microscope of the present invention, it is desirable that the pupil modulation means is a Hofmann module.

In the microscope of the present invention, the pupil modulation means is constructed to be movable in and out of the optical path.

In the microscope of the present invention, it is desirable to include a fluorescence cube having at least the dichroic mirror and the barrier filter cutting off unwanted light, of light from the specimen, and a turret on which the fluorescence cube and the pupil modulation means are arranged, switchable with respect to an insertion and removal of the fluorescence cube or the pupil modulation means in and out of the optical path between the relay optical system and the imaging lens so that the fluorescence cube or the pupil modulation means, when inserted in the optical path between the relay optical system and the imaging lens, is placed in the proximity of a position conjugate with the pupil position of the objective lens, formed between the relay optical system and the imaging lens.

In the microscope of the present invention, it is desirable to include a fluorescence cube having at least the dichroic mirror and the barrier filter cutting off unwanted light, of light from the specimen, and a slider on which the fluorescence cube and the pupil modulation means are arranged, switchable with respect to an insertion and removal of the fluorescence cube or the pupil modulation means in and out of an optical path between the relay optical system and the imaging lens so that the fluorescence cube or the pupil modulation means, when inserted in the optical path between the relay optical system and the imaging lens, is placed in the proximity of a position conjugate with the pupil position of the objective lens, formed between the relay optical system and the imaging lens.

In the microscope of the present invention, it is desirable to include a plurality of fluorescence cubes, each having at least the dichroic mirror and the barrier filter cutting off unwanted light, of light from the specimen, a first turret on which the plurality of fluorescence cubes are arranged, switchable with respect to an insertion and removal of each of the plurality of fluorescence cubes in and out of an optical path between the relay optical system and the imaging lens, and a second turret on which a plurality of pupil modulation means are arranged, switchable with respect to an insertion and removal of each of the plurality of pupil modulation means in and out of the optical path between the relay optical system and the imaging lens so that one of the fluorescence cubes and one of the pupil modulation means, when inserted in the optical path between the relay optical system and the imaging lens, are arranged in the proximity of a position conjugate with the pupil position of the objective lens, formed between the relay optical system and the imaging lens.

In the microscope of the present invention, it is desirable to include a plurality of fluorescence cubes, each having at least the dichroic mirror and the barrier filter cutting off unwanted light, of light from the specimen, a first slider on which the plurality of fluorescence cubes are arranged, switchable with respect to an insertion and removal of each of the plurality of fluorescence cubes in and out of the optical path between the relay optical system and the imaging lens, and a second slider on which a plurality of pupil modulation means are arranged, switchable with respect to an insertion and removal of each of the plurality of pupil modulation means in and out of the optical path between the relay optical system and the imaging lens so that one of the fluorescence cubes and one of the pupil modulation means, when inserted in the optical path between the relay optical system and the imaging lens, are arranged in the proximity of a position conjugate with the pupil position of the objective lens, formed between the relay optical system and the imaging lens.

In the microscope of the present invention, it is desirable to include a plurality of pupil modulation means, each having a phase film at a different position in the direction of the optical axis, in accordance with a plurality of objective lenses having different pupil positions.

In the microscope of the present invention, it is desirable to include a plurality of objective lenses of identical pupil positions, but of different magnifications, and a plurality of pupil modulation means, each having the phase film at an identical position in the direction of the optical axis.

In the microscope of the present invention, it is desirable that an image restriction means for partially blocking illumination light from the reflecting fluorescence illumination optical system is constructed to be locatable in the proximity of an imaging position where an intermediate image of the specimen is formed through the relay optical system.

In the microscope of the present invention, it is desirable that the image restriction means is a rotatable Nipkow disk.

In the microscope of the present invention, it is desirable that the image restriction means is a rotatable slit member.

In the microscope of the present invention, it is desirable that the image restriction means is constructed so that an aperture through which illumination light from the reflecting fluorescence illumination optical system is able to pass is configured into a rectangular shape corresponding to a shape of an image pickup surface of the image sensor.

In the microscope of the present invention, it is desirable that a deflection member deflecting an optical path from the objective lens to the imaging lens in a nearly horizontal direction is located at a preset place between the objective lens and the relay optical system.

In the microscope of the present invention, it is desirable that a split means splitting the optical path into an optical path picked up by the image sensor and an optical path for visual observation is provided at a preset position on the optical path from the objective lens to the imaging lens, deflected through the deflection member.

In the microscope of the present invention, it is desirable that an autofocus correction mechanism is provided between the objective lens and the imaging lens.

According to the microscope of the present invention, the microscope is obtained in which the amount of light for forming an image in the image pickup area and the amount of light for illumination in the observation region can be equalized and the amount of light is efficiently utilized to be switchable to various observations.

BRIEF DESCRIPTION OF THE DRAWINGS

FIGS. 13A-13C are explanatory views showing an optical structure placed in the proximity of a pupil position conjugate with the pupil position of the objective lens in the microscope according to Embodiment 10 of the present invention, in which FIG. 13A is a plan view, looking from the objective lens side, FIG. 13B is a side view of FIG. 13A, and FIG. 13C is a perspective view of FIG. 13A, looking from the objective lens side.

FIG. 19A shows a rotatable Nipkow disk, FIG. 19B shows a rotatable slit member, and FIG. 19C shows an aperture stop having a rectangular aperture corresponding to the shape of the image sensor 3.

FIG. 21A is a side view showing the two turrets, FIG. 21B is a plan view of the turret A holding fluorescence cubes, and FIG. 21C is a plan view of the turret B holding the pupil modulation modules.

BEST MODE FOR CARRYING OUT THE INVENTION

Before undertaking the description of embodiments, the function and effect of the present invention will be explained.

Figure 2:
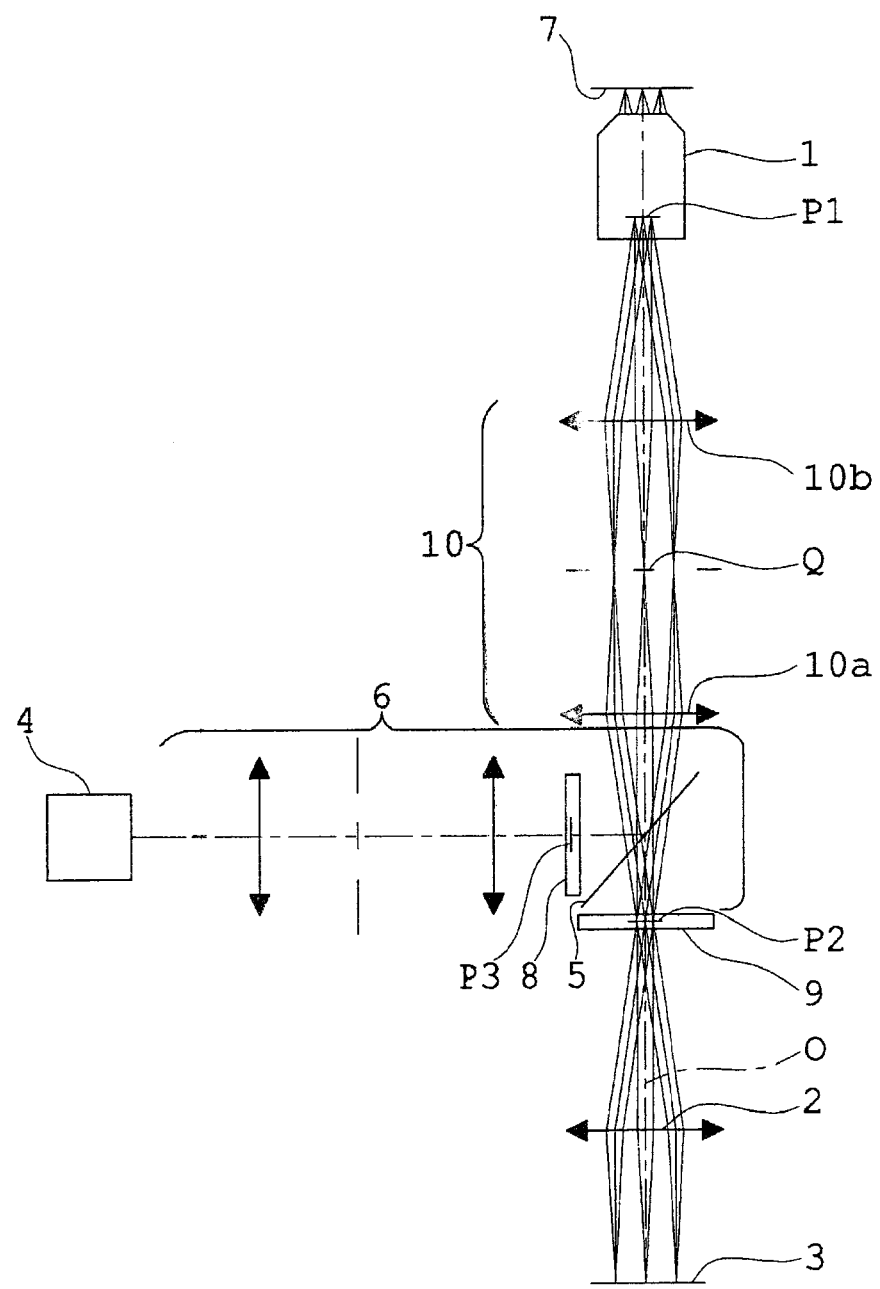
FIG. 2 is a conceptual view showing an example of a fundamental optical arrangement in the microscope of the present invention.

FIG. 2 is a conceptual view showing an example of a fundamental optical arrangement in the microscope of the present invention. The microscope shown in FIG. 2 has an objective lens 1, an imaging lens 2, an image sensor 3, an illumination light source 4, and a reflecting fluorescence illumination optical system 6. Also, in FIG. 2, reference symbol P1 represents the pupil position of the objective lens 1, P2 and P3 represent pupil positions conjugate with the pupil position P1, and O represents the center axis of the objective lens 1 and the imaging lens 2. The imaging lens 2 is constructed so that light passing through the objective lens 1 is projected to form the image of a specimen 7. The image sensor 3 is placed at the imaging position where the image of the specimen 7 is formed by the imaging lens 2. The reflecting fluorescence illumination optical system 6 is designed to have a dichroic mirror 5 introducing light from the illumination light source 4 into the optical path on the objective-lens-1 side and to irradiate the specimen 7 with the light.

Figure 1:
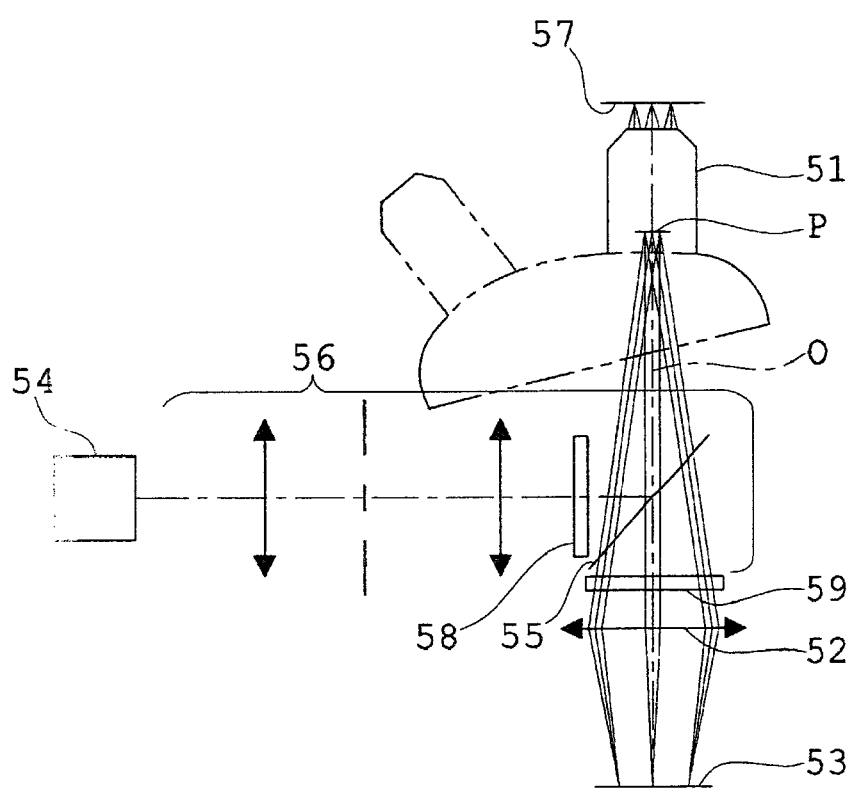
FIG. 1 is a conceptual view showing an example of a fundamental optical arrangement in a conventional microscope.

Further, the microscope shown in FIG. 2, in contrast with the conventional microscope such as that shown in FIG. 1, has a relay optical system 10 that includes relay lenses 10a and 10b for forming an intermediate image of the specimen 7, between the objective lens 1 and the imaging lens 2, to relay the image to the imaging lens 2. also, reference symbol Q denotes the imaging position of the intermediate image. The dichroic mirror 5 is interposed between the pupil position P2 that is conjugate with the pupil position P1 of the objective lens 1 and that is formed between the relay optical system 10 and the imaging lens 2, and the relay optical system 10. Also, in FIG. 2, reference numeral 9 denotes a barrier filter cutting off unwanted light, of light from the specimen 7.

When the microscope is constructed as mentioned above, the marginal beam can be prevented from separating from the central beam in going from the objective lens 1 to the imaging lens 2 through the relay optical system 10. Consequently, even though the optical path between the objective lens 1 and the imaging lens 2 is elongated, the eclipse of light passing through the peripheries of the barrier filter 9 and the dichroic mirror 5 can be eliminated and the problem of the insufficiency of the amount of light imaged on the periphery of the image pickup surface of the image sensor 3 is solved so that the amount of light imaged in the entire image pickup area is uniformed and the quantification and reproducibility of a fluorescent image thus obtained can be improved. Similarly, in excitation light with which the specimen is illuminated, the eclipse of light due to the excitation filter 8 and the dichroic mirror 5 can also be eliminated. Whereby, in the fields of biology and medicine, when a lesion part is diagnosed with colors of cells imaged by carrying out the fluorescence observation under the microscope or when a time-lapse observation is made, the possibility of lesion relative to cells captured on the periphery and the quantification, such as a change of a luminance signal, of the fluorescent image of a diagnostic object moving within an imaging region can be correctly recognized without a positional dependence in the plane of the image.

When the dichroic mirror 5 is interposed between the pupil position P2 conjugate with the pupil position P1 of the objective lens 1 and the relay optical system 10, the marginal beam passing through the barrier filter 9 placed in the proximity of the dichroic mirror 5 can be brought close to the central beam. As a result, a part of the marginal beam does not miss the barrier filter 9, so that the brightness and wavelength of fluorescent light imaged on the image pickup surface of the image sensor 3 through the imaging lens 2 are uniformed with respect to the center and periphery of the image pickup surface and the quantification and reproducibility of a fluorescent image thus obtained can be improved.

Similarly, the marginal beam incident on the excitation filter 8 can be brought close to the central beam and a part of the marginal beam does not miss the excitation filter 8, so that the brightness and wavelength of excitation light irradiating the surface of the specimen 7 through the objective lens 1 are uniformed with respect to the center and periphery of the irradiated surface and the quantification and reproducibility of a fluorescent image thus obtained can be improved.

As a result, in the reflecting fluorescence illumination optical system 6, light from the light source is not eclipsed through the excitation filter 8 with respect to the pupil of the objective lens and it becomes possible to illuminate the specimen with uniform excitation light, so that the unevenness and intensity of illumination of the excitation light on the surface of the specimen are homogenized and the quantification and reproducibility are improved.

In contrast with the conventional reflecting fluorescence illumination optical system, the eclipse due to the excitation filter 8 is prevented and the projection magnification of the light source in the reflecting fluorescence illumination optical system can be increased, with the result that the efficiency of utilization of the light source 4 can be improved.

In the microscope shown in FIG. 2, the dichroic mirror 5 is placed in the proximity of the pupil position P2 conjugate with the pupil position P1 of the objective lens 1.

When the optical arrangement is made as mentioned above, the marginal beam passing through the dichroic mirror 5 can be brought close to the central beam as far as possible, and it becomes easier to obtain eclipse-free and uniformed illumination light and a photographic image. In particular, this arrangement is suitable for the case where the dichroic mirror 5 is combined with the excitation filter 8 and the barrier filter 9 to constitute a unit such as the fluorescence cube. For example, the barrier filter 9 is located at the pupil position P2 conjugate with the pupil position P1 of the objective lens 1 and thereby the marginal beam passing through the barrier filter 9 can be brought closest to the central beam. Similarly, the excitation filter 8 is located at the pupil position P3 conjugate with the pupil position P1 of the objective lens 1 and thereby the beam passing through the excitation filter 8 can be brought closest to the central beam.

The microscope shown in FIG. 2 is constructed so that a light beam from the specimen 7 is nearly afocal at the pupil position P2 conjugate with the pupil position P1 of the objective lens 1. By doing so, even when the optical path is elongated, the marginal beam can be prevented from separating extremely from the center and hence it becomes easy to obviate the eclipse of the marginal beam.

Figure 16B:
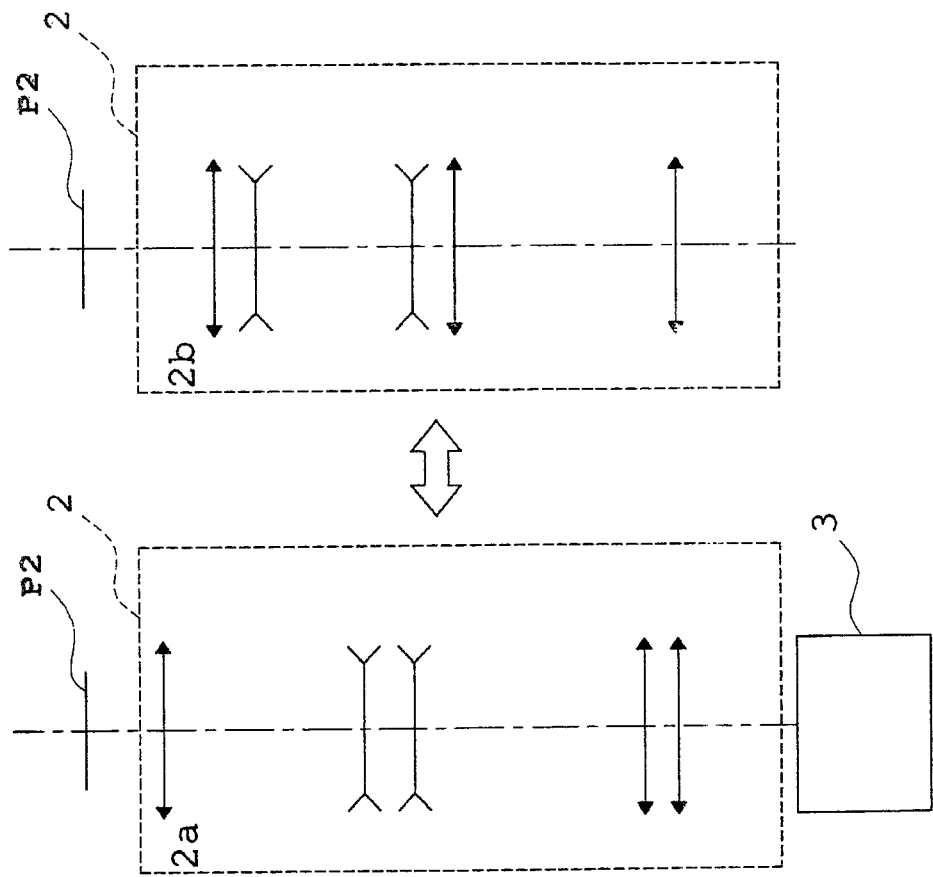
FIGS. 16A-16B are schematic diagrams that show configuration examples of the imaging lens 2 in the microscope shown in FIG. 2.
Figure 16A:
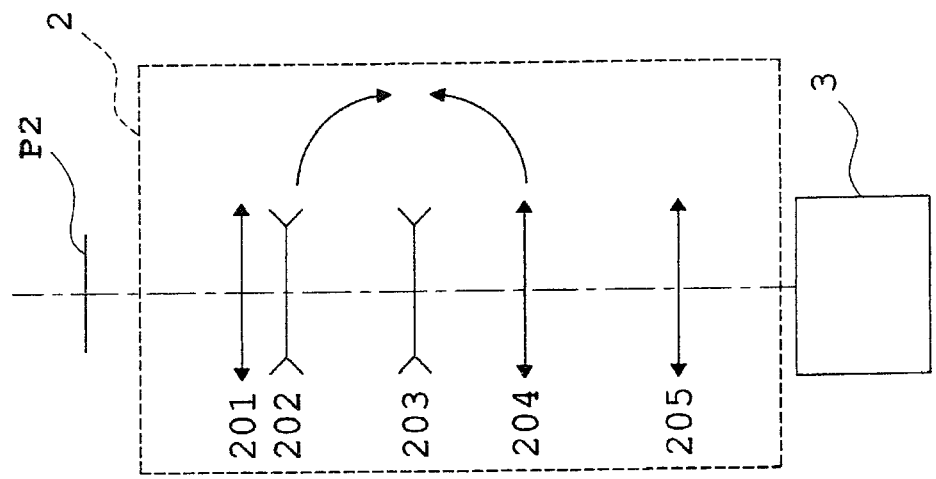

It is desirable that the imaging lens 2 is constructed with an imaging optical system provided with a zoom optical system or a variable magnification optical system whose magnification is changed stepwise. An example of the imaging lens with a zoom optical system is shown in FIG. 16A. In this example, the imaging lens 2 is formed as a zoom optical system including lenses 201, 202, 203, 204 and 205, where the lenses 202 and 204 are configured to be movable along the optical axis for zooming. An example of the variable magnification optical system with stepwise magnification change is shown in FIG. 16B. In this example, the imaging lens 2 includes a low magnification imaging lens 2a and a high magnification imaging lens 2b so that a selected one of them is inserted in the optical path. When the imaging optical system provided with the zoom optical system or the variable magnification optical system whose magnification is changed stepwise is used, various observation magnifications can be accommodated.

Also, in this case, it is desirable to satisfy the following condition:

$$0.6 \leq |\beta| \leq 1.5$$

where $\beta$ is the pupil relay magnification of the relay optical system from the pupil position P1 of the objective lens to the pupil conjugate position P2.

Beyond the upper limit of the above condition, the eclipse of the marginal light due to the barrier filter 9 becomes liable to occur. On the other hand, below the lower limit of the condition, the angle of incidence of light emerging from the relay optical system on the barrier filter 9 increases significantly and a spectral property is impaired by undergoing the influence of the dependence of the barrier filter 9 on the angle of incidence.

Also, the following equation should more preferably be satisfied:

$$\beta \approx -1$$

In the microscope shown in FIG. 2, it is desirable that a fly-eye lens (omitted from the figure) is placed in the proximity of the pupil position P3 conjugate with the pupil position P1 of the objective lens 1 in the reflecting fluorescence illumination optical system 6. By such an arrangement, a Köhler illumination system which does not depend on the light-distribution angle characteristic or the luminance distribution characteristic of the light source can be constructed, and the reflecting fluorescence illumination optical system 6 in which uneven illumination on the surface of the specimen is made more uniform and the dependence of the light source on the light-distribution angle is slight can be constructed.

In the microscope shown in FIG. 2, it is desirable that the illumination light source 4 is constructed with a reflector light source, an LED light source, or a fiber light source. When the reflector light source is used, the amount of light of the illumination light source 4 can be efficiently utilized. When the LED light source is used, a long-time observation does not cause damage to an observation object, and a preset wavelength can be used for irradiation in accordance with the application.

It is also desirable that an integrator rod (omitted from the figure) is provided in the reflecting fluorescence illumination optical system 6. The integrator rod is constructed in the shape of a square-column glass rod so that light incident on the integrator rod from the light source repeats total reflection in turn and thereby is mixed and illumination distribution is uniformed. By providing critical illumination that the exit end face of the integrator rod is projected on the surface of the specimen, light from the illumination light source 4 can be uniformed.

It is further desirable that the integrator rod is constructed so that its square-column shape is similar to the image pickup area. In addition to the glass rod shape, the integrator rod may be constructed with a light pipe in which the square column is hollow and is constructed with a mirror.

In the microscope shown in FIG. 2, the objective optical system 1, the imaging optical system 2, and the relay optical system 10 are constructed to be nearly telecentric optical systems on the surface of the object, at the position of the intermediate image, and on the surface of the image sensor, respectively. By such an arrangement, angles of rays from the center to the periphery are equalized and the phenomenon of shading inherent in the image sensor is suppressed so that the uniformity of the amount of light can be ensured.

In the microscope shown in FIG. 2, a pupil modulation means may be placed in the proximity of the pupil position P2 conjugate with the pupil position P1 of the objective lens 1, formed between the relay optical system 10 and the imaging lens 2.

In the microscope, observations based on various observation techniques of a phase contrast observation and a differential interference observation, in addition to a fluorescence microscope observation, are sometimes required. In such cases, when the pupil modulation means is placed instead of the barrier filter 9 in the fluorescence observation, high-precision observation images in which the amounts of light are equalized are obtained with respect to various observations. Specifically, it is desirable that the pupil modulation means is constructed with a variable stop. By such an arrangement, the depth of focus of the specimen 7 can be adjusted and, for example, even though a number of sample vessels arranged have individual variations in thickness, the diameter of the variable stop is adjusted and thereby a specimen image at an image quality level that the focus is stable can be obtained. As another effect, with respect to the loss of the amount of light due to vignetting inherent in the objective lens in other observation techniques as well as in the fluorescence observation, the aperture stop is adjusted and thereby, although an effective numerical aperture becomes smaller than the numerical aperture of the objective lens, the loss of the amount of marginal light due to the objective lens is eliminated and the amounts of central and marginal light can be equalized.

Figure 18:
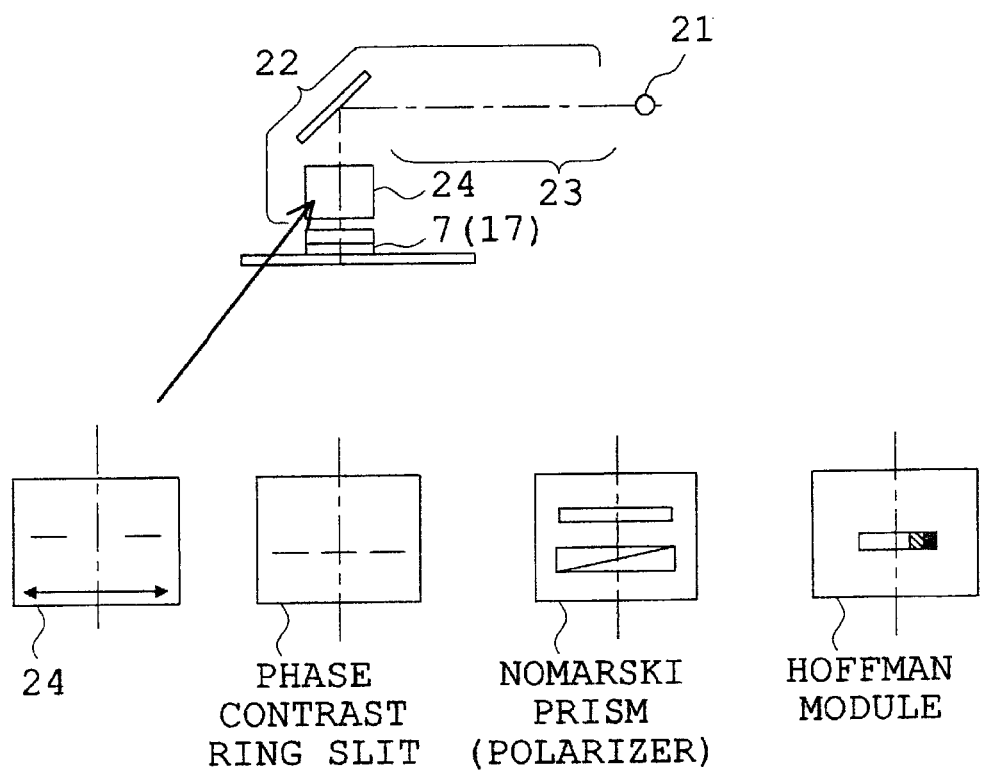
FIG. 18 is a schematic diagram that shows a transmitting illumination system to be used with the pupil modulation means that is arranged at a position proximate to the pupil position P2 (P12) in the microscope shown in FIG. 2 or FIG. 3.

It is desirable that the pupil modulation means is constructed with a member in which a phase film is zonally provided, upon a transmitting illumination system being added to the microscope of FIG. 2 to irradiate the specimen 7 with zonal illumination light corresponding to the member in which the phase film is zonally provided. Such a transmitting illumination system is shown in FIG. 18. Here, the transmitting illumination system is formed of a transmitting illumination light source 21 and a transmitting illumination optical system 22. When the member in which a phase film is zonally provided is inserted at a position proximate to the pupil position P2, a phase contrast ring slit is inserted in a condenser 24 of the illumination optical system 22, to provide zonal illumination light. By doing so, a high-precision phase contrast observation in which the amount of light is uniformed can be carried out over the entire image pickup surface.

The pupil modulation means may be constructed with a Nomarski prism. By doing so, a high-precision phase contrast observation in which the amount of light is uniformed can be carried out over the entire image pickup surface.

Figure 17:
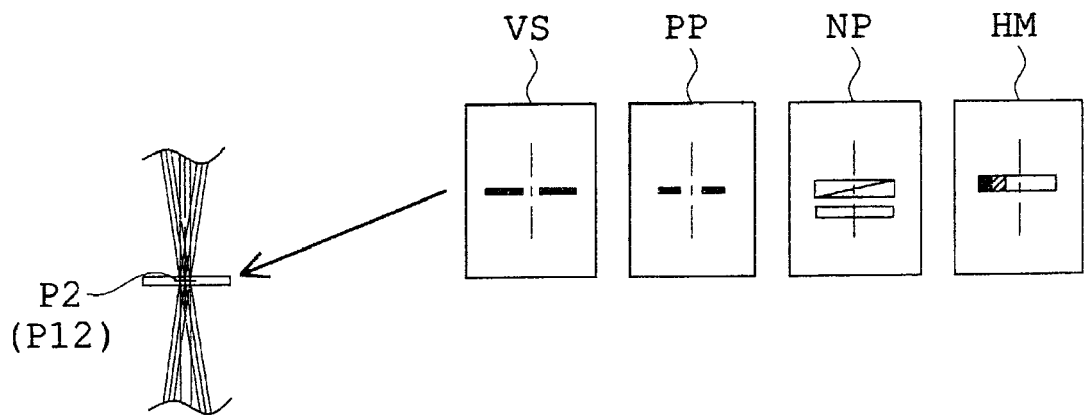
FIG. 17 is a schematic diagram that shows a configuration example in which pupil modulation means is arranged at a position proximate to the pupil position P2 (P12) in the microscope shown in FIG. 2 or FIG. 3.

The pupil modulation means may also be constructed with a Hofmann module. Also, it is desirable that the pupil modulation means is designed to be movable in and out of the optical path. By such an arrangement, observations based on various observation techniques can be carried out over the entire image pickup surface with a simple operation and with a high degree of accuracy. An example of such an arrangement is shown in FIG. 17. In this configuration, selected one of a variable stop VS, a phase plate PP in which a phase film is zonally provided, a Nomarski prism NP and a Hoffman module HM can be inserted, in place of the barrier filter 9, in the optical path at a position proximate to the pupil position P2 in the microscope of FIG. 2, in accordance with a selected observation mode.

Figure 19A:
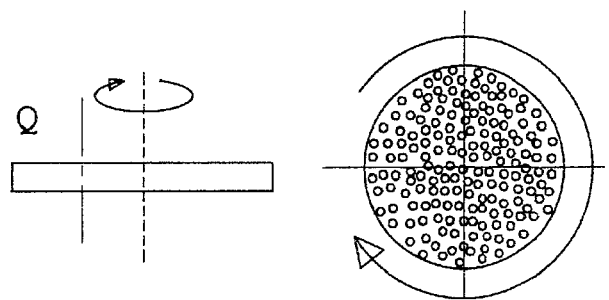
FIGS. 19A-19C are schematic diagrams that show examples of image restriction means that can be arranged at the position Q in the microscope of FIG. 2 or FIG. 3, where

In the microscope shown in FIG. 2, it is desirable that an image restriction means for partially blocking illumination light from the reflecting fluorescence illumination optical system 6 is constructed to be locatable in the proximity of the imaging position Q of the intermediate image of the specimen 7 formed through the relay optical system 10. Specifically, it is desirable that the image restriction means is a rotatable Nipkow disk as shown in FIG. 19A. By doing so, a confocal microscope which is suitable for the physiological reaction observation and morphology observation of the cell can be constructed.

Figure 19B:
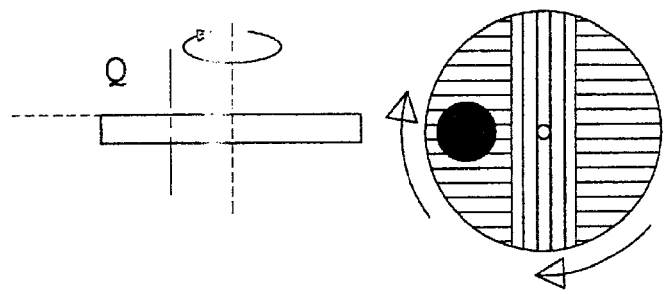

It is also desirable that the image restriction means is a rotatable slit member as shown in FIG. 19B. By doing so, only light from a focal plane passes through the slit member and blurred images before and behind the focal plane are cut off by the slit member so that an image in which blurring is eliminated in the entire image pickup area is obtained.

Figure 19C:

In the image restriction means, it is desirable that an aperture, through which illumination light from the reflecting fluorescence illumination optical system 6 can pass, is configured into a rectangular shape corresponding to the shape of the image pickup surface of the image sensor 3, as shown in FIG. 19C. By doing so, irradiation to the specimen 7 can be restricted within a necessary limit and damage to the specimen 7 and fluorescence bleaching can be kept to a minimum.

Further, in the microscope of FIG. 2, it is desirable that a deflection member, such as a mirror, deflecting an optical path from the objective lens 1 to the imaging lens 2 in a nearly horizontal direction is located at a preset place between the objective lens 1 and the relay optical system 10. By such an arrangement, when the microscope is constructed to have an eyepiece optical system for making a visual observation, a vertical length of the microscope can be kept by bending the optical path in the horizontal direction, and hence a viewer is capable of making the observation in a natural position.

In this case, it is desirable that a split means splitting the optical path into an optical path picked up by the image sensor and an optical path for visual observation is provided at a preset position on the optical path from the objective lens 1 to the imaging lens 2, deflected through the deflection member. When an arrangement is made in this way, the microscope in which the image of the specimen 7 picked up can be observed by a display device and in addition, an observation with the naked eye can also be made in a natural position is obtained.

In the microscope shown in FIG. 2, when an autofocus correction mechanism (omitted from the figure) is provided between the objective lens 1 and the imaging lens 2, a sharp observation image is obtained without performing the manual operation of focus adjustment. This is further desirable. In this case, when the microscope shown in FIG. 2 is available, the specimen is illuminated with light of infrared wavelength used for focal position detection, through the objective lens, and the focal position can be detected with high accuracy through a light-receiving element provided in the autofocus correction mechanism by reflected light from the surface or vessel surface of the specimen. Also, in the autofocus correction mechanism, any mechanism that the specimen is irradiated with light of a preset wavelength and reflected light from the specimen is received so that the focal position can be corrected in accordance with a light-received state is applicable.

Also, in the microscope shown in FIG. 2, light emanating from the specimen 7 can also be observed without making illumination light emerge from the light source 4. In this case as well, the marginal beam can be prevented from separating from the central beam in going from the objective lens 1 to the imaging lens 2 through the relay optical system 10. Consequently, even though the optical path between the objective lens 1 and the imaging lens 2 is elongated, the eclipse of light passing through the peripheries can be eliminated and the problem of the insufficiency of the amount of light imaged on the periphery of the image pickup surface of the image sensor 3 is solved so that the amount of light imaged in the entire image pickup area can be uniformed.

First Aspect

In accordance with the drawings, the aspect of the microscope of the present invention will be explained below.

Figure 3:
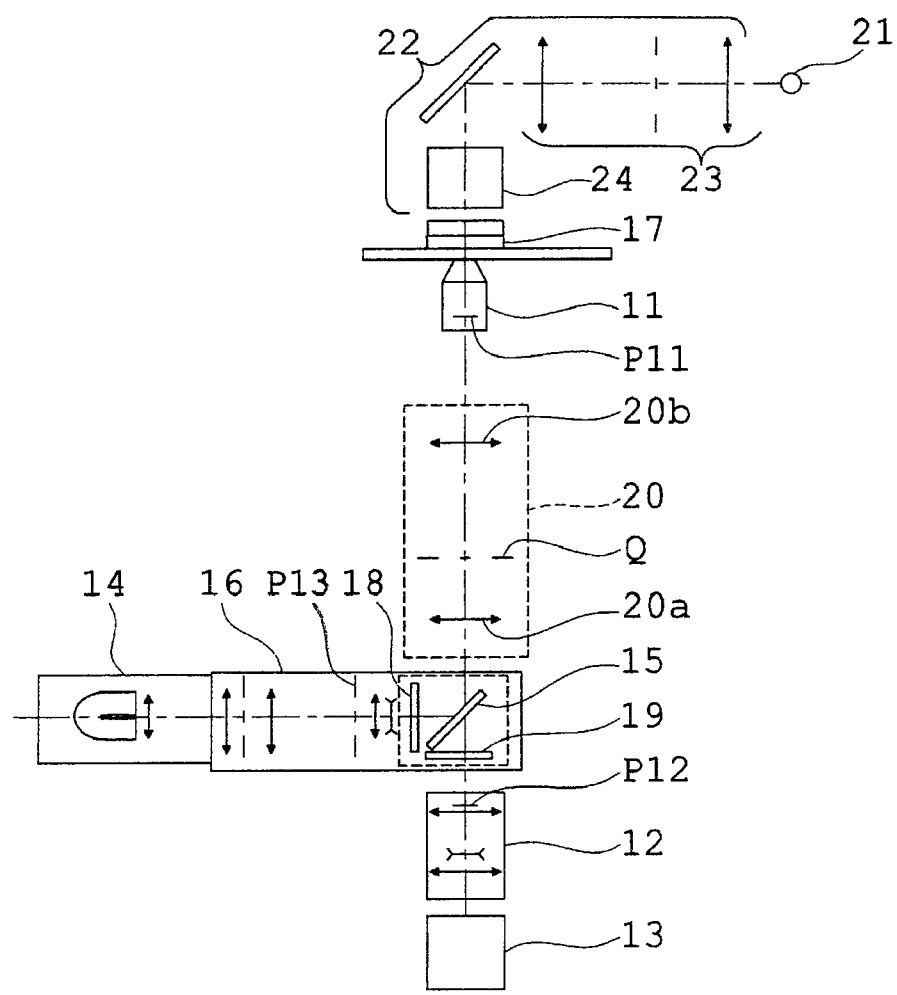
FIG. 3 is an explanatory view showing a schematic structure of the whole of the microscope according to a first aspect of the present invention.

FIG. 3 is an explanatory view showing a schematic structure of the whole of the microscope according to the first aspect of the present invention. The microscope of the first aspect has an objective lens 11, an imaging lens 12, an image sensor 13, an illumination light source 14, a reflecting fluorescence illumination optical system 16, a transmitting illumination light source 21, and a transmitting illumination optical system 22. The transmitting illumination light source 21 and the transmitting illumination optical system 22 form a transmitting illumination system. Also, in FIG. 3, reference symbol P11 represents the pupil position of the objective lens 11, P12 and P13 represent pupil positions conjugate with the pupil position P11, and O represents the center axis of the objective lens 11 and the imaging lens 12. The imaging lens 12 is designed so that light passing through the objective lens 11 is projected to form the image of a specimen 17. The image sensor 13 is constructed with a CCD camera and is placed so that its image pickup surface is located at the imaging position where the image of the specimen 17 is formed by the imaging lens 12. The illumination light source 14 is constructed with a reflector light source. Also, it may be constructed with an LED light source or a fiber light source (omitted from the figure). The reflecting fluorescence illumination optical system 16 is designed to have a dichroic mirror 15 introducing light from the illumination light source 14 into the optical path on the objective-lens-11 side and to illuminate the specimen 17 with the light. The transmitting illumination optical system 22 is constructed with a transmitting illumination lens 23 and a condenser lens 24.

The microscope of the first aspect further has a relay optical system 20 forming an intermediate image of the specimen 17 to relay the image to the imaging lens 12, between the objective lens 11 and the imaging lens 12. Also, reference symbol Q denotes the imaging position of the intermediate image. The dichroic mirror 15 is placed between the pupil position P12 conjugate with the pupil position P11 of the objective lens 11, formed between the relay optical system 20 and the imaging lens 12, and the relay optical system 20 and in the proximity of the pupil position 12.

A barrier filter 19 is placed in the proximity of the pupil position P12. In the proximity of the pupil position P13 conjugate with the pupil position P11 of the objective lens 11, an excitation filter 18 is placed.

Also, it is desirable that the barrier filter 19 is located at the pupil position P12. When an arrangement is made in this way, a light beam passing through the barrier filter 19 can be made smallest. Likewise, it is desirable that the excitation filter 18 is located at the pupil position P13. When an arrangement is made in this way, a light beam passing through the excitation filter 18 can be made smallest. The dichroic mirror 15, the excitation filer 18, and the barrier filter 19 are constructed as a single cubic unit to be movable in and out of the optical path. The imaging lens 12 is constructed with an imaging optical system provided with a zoom optical system so that a light beam from the specimen 17 is nearly afocal at the pupil position P12. Also, instead of using the zoom optical system, it is possible to use a variable magnification optical system (as shown in FIG. 16B) whose magnification is changed stepwise, constructed so that, for example, a turret or a slider provided with lenses of different magnifications is rotated or slid and thereby a lens of a desired magnification can be placed on the optical path.

The relay optical system 20 is designed to satisfy the following condition:

$$0.6 \leq |\beta| \leq 1.5$$

where $\beta$ is a pupil relay magnification.

The objective optical system 11, the imaging optical system 12, and the relay optical system 20 are constructed to be nearly telecentric optical systems on the surface of the object, at the position of the intermediate image, and on the surface of the image sensor, respectively. The microscope of the first aspect is constructed so that a fly-eye lens (omitted from the figure) can be located at the pupil position P13 in the reflecting fluorescence illumination optical system 16. Also, the microscope may be constructed to have an integrator rod (omitted from the figure) in the reflecting fluorescence illumination optical system 16.

Moreover, the microscope of the first aspect is constructed so that a pupil modulation mean can be placed in the proximity of the pupil position P12 to be movable in and out of the optical path. As the pupil modulation means, for example, a phase plate PP (as shown in FIG. 17) in which a phase film is zonally provided can be used. In this case, as shown in FIG. 18, the condenser lens 24 of the transmitting illumination optical system 22 is provided with a ring-shaped slit to function as a condenser for phase contrast microscopy, so that the specimen 17 can be irradiated with zonal illumination light corresponding to the phase plate. By doing so, the phase contrast observation can be carried out.

Also, as other pupil modulation means in the microscope of the first aspect, for example, a variable stop VS, a Nomarski prism NP, and a Hofmann module HM are applicable. The microscope of the first aspect is constructed so that an image restriction means for partially blocking illumination light from the reflecting fluorescence illumination optical system 16 can be located in the proximity of the imaging position Q where the intermediate image of the specimen 17 is formed through the relay optical system 20. As the image restriction means, a rotatable Nipkow disk (shown in FIG. 19A) and a rotatable slit member (shown in FIG. 19B) can be used.

Also, it is desirable that when the Nipkow disk or the rotatable slit member is placed at the position g of the intermediate image, a nearly telecentric optical system is constructed. Alternatively, as the image restriction means, it is also possible to use a light blocking member (shown in FIG. 19C) that has an aperture, through which illumination light from the reflecting fluorescence illumination optical system 16 can pass, configured into a rectangular shape corresponding to the shape of the image pickup surface of the image sensor 13.

Also, it is desirable that when zoom and variable magnification functions are imparted to the imaging optical system 12, the size of the aperture of the image restriction means is made variable in accordance with an imaging magnification. By making the size of the aperture variable, an area in which the specimen is irradiated with excitation light is kept to a minimum and the influence of bleaching of the specimen can be lessened.

Figure 20:
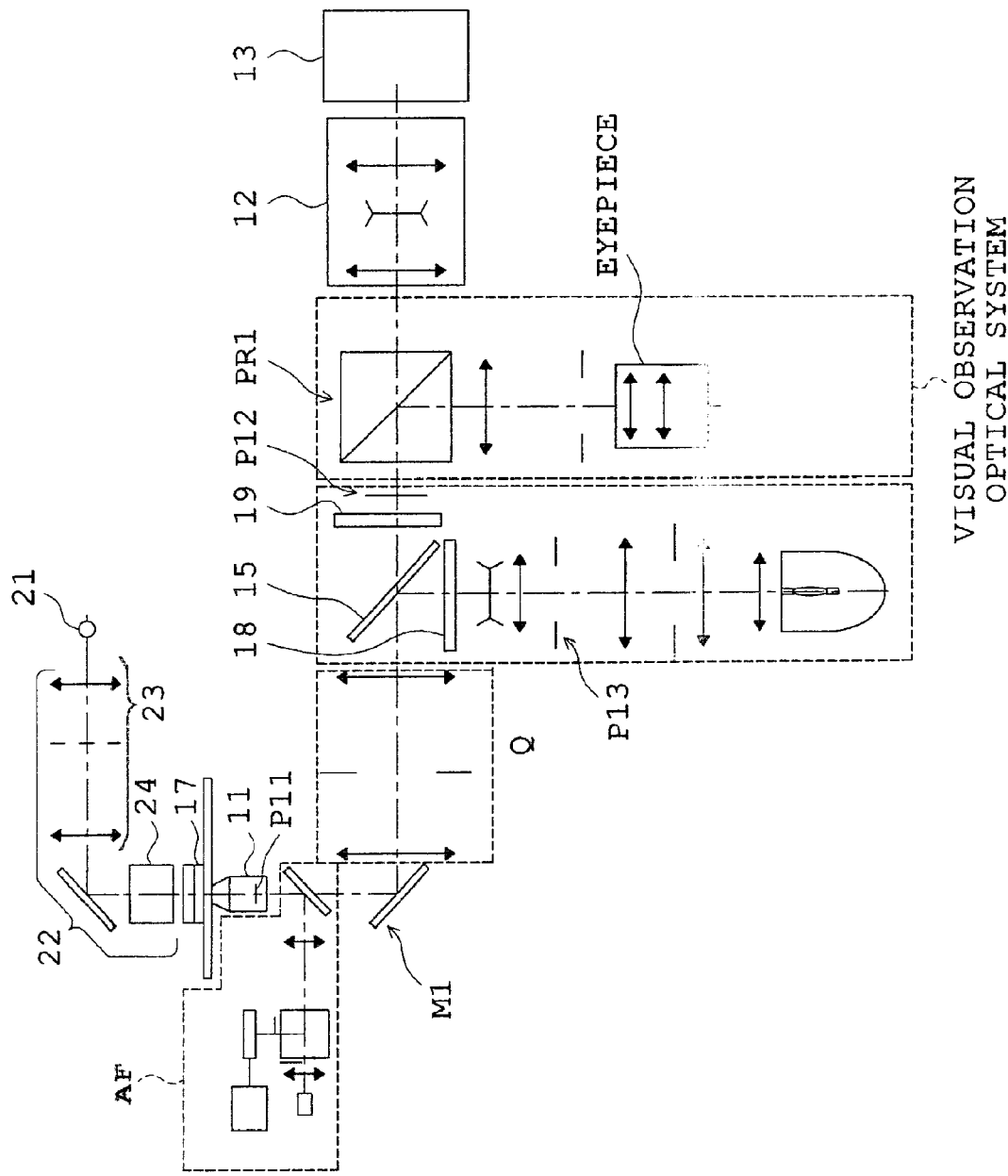
FIG. 20 is a schematic diagram that shows the configuration in which a deflection member, a path splitting member, and an autofocus correction mechanism are added to the microscope shown in FIG. 3.

In the microscope of the first aspect, it is further desirable that, as shown in FIG. 20, a deflection member M1 such as a mirror, deflecting an optical path from the objective lens 11 to the imaging lens 12 in a nearly horizontal direction is located at a preset place between the objective lens 11 and the relay optical system 20. In this case, it is desirable that a split means PR1 for splitting the optical path into an optical path to be picked up by the image sensor 13 and an optical path for visual observation is provided at a preset position on the optical path from the objective lens 11 to the imaging lens 12, deflected through the deflection member M1.

Moreover, as shown in FIG. 20, the microscope of the first aspect is such that an autofocus correction mechanism AF can also be provided between the objective lens 11 and the imaging lens 12. Also, in the autofocus correction mechanism AF, any mechanism that the specimen 17 is irradiated with light of a preset wavelength and reflected light from the specimen is received so that the focal position can be corrected in accordance with a light-received state is applicable.

According to the microscope of the first aspect constructed as mentioned above, for example, in the arrangement of FIG. 3 showing the case where the fluorescence observation is made, light emitted from the illumination light source 14 is incident on the reflecting fluorescence illumination optical system 16, is changed into light of excitation wavelength alone through the excitation filter 18 in the reflecting fluorescence illumination optical system 16 to enter the dichroic mirror 15, is reflected by the dichroic mirror 15 to enter the relay optical system 20, is condensed at the imaging position Q where the intermediate image is formed through a relay optical system 20a, and is made to emerge as a nearly parallel beam through a relay optical system 20b to enter the objective lens 11 so that the light source is projected in the proximity of the pupil position P11 of the objective lens 11 through the reflecting fluorescence illumination optical system 16 and the specimen 17 is irradiated through the objective lens 11. Light from the specimen 17 containing fluorescence passes through the objective lens 11 to enter the relay optical system 20, is imaged at the imaging position Q where the intermediate image is formed through the relay optical system 20b, is made emerge as a nearly parallel beam through the relay optical system 20a to enter the dichroic mirror 15, is transmitted through the dichroic mirror 15 to enter the barrier filter 19, is incident on the imaging lens 12 after unwanted wavelengths other than desired fluorescent light are cut off through the barrier filter 19, and is formed as the image of the specimen 17 on the image pickup surface of the image sensor 13 through the imaging lens 12 so that the image is picked up by the image sensor 13. The image of the specimen 17 picked up by the image sensor 13 can be observed as a picture through a display device omitted from the figure.

In this case, according to the microscope of the first aspect, a marginal beam can be prevented from separating from a central beam in going from the objective lens 11 to the imaging lens 12 through the relay optical system 20. Consequently, even though the optical path between the objective lens 11 and the imaging lens 12 is elongated, the eclipse of light passing through the peripheries of the barrier filter 19 and the dichroic mirror 15 can be eliminated and the problem of the insufficiency of the amount of light imaged on the periphery of the image pickup surface of the image sensor 13 is solved so that the amount of light imaged in the entire image pickup area can be uniformed. Whereby, in the fields of biology and medicine, when a lesion part is diagnosed with colors of cells imaged by carrying out the fluorescence observation under the microscope or when a time-lapse observation is made, the possibility of lesion relative to cells captured on the periphery and the quantification, such as a change of a luminance signal, of the fluorescent image of a diagnostic object moving within an imaging region can be correctly recognized without a positional dependence in the plane of the image.

Since the dichroic mirror 15 is interposed between the pupil position P12 conjugate with the pupil position P11 of the objective lens 11 and the relay optical system 20, the marginal beam passing through the barrier filter 19 placed in the proximity of the dichroic mirror 15 can be brought close to the central beam. As a result, a part of the marginal beam does not miss the barrier filter 19, so that the brightness and wavelength of fluorescent light imaged on the image pickup surface of the image sensor 13 through the imaging lens 12 are uniformed with respect to the center and periphery of the image pickup surface. Similarly, the marginal beam incident on the excitation filter 18 can be brought close to the central beam and a part of the marginal beam does not miss the excitation filter 18, so that the brightness and wavelength of excitation light irradiating the surface of the specimen 17 through the objective lens 11 are uniformed with respect to the center and periphery of the irradiated surface and the quantification and reproducibility of a fluorescent image thus obtained can be improved. In contrast with the conventional reflecting fluorescence illumination optical system, the eclipse due to the excitation filter 18 is prevented and the magnification of light source projection of the reflecting fluorescence illumination optical system 16 can be increased, with the result that the efficiency of utilization of the light source 14 can be improved.

Furthermore, since the dichroic mirror 15 is placed in the proximity of the pupil position P12 conjugate with the pupil position P11 of the objective lens 11, the marginal beam passing through the dichroic mirror 15 can be brought close to the central beam as far as possible, and it becomes easier to obtain eclipse-free and uniformed illumination light and a photographic image. This arrangement is suitable for the case where the dichroic mirror 15 is combined with the excitation filter 8 and the barrier filter 9 to constitute a unit such as the fluorescence cube. Also, when the barrier filter 19 is located at the pupil position P12 conjugate with the pupil position P11 of the objective lens 11, the most favorable arrangement is obtained. By doing so, the marginal beam passing through the barrier filter 19 can be brought closest to the central beam. Similarly, when the excitation filter 18 is located at the pupil position P13 conjugate with the pupil position P11 of the objective lens 11, the most favorable arrangement is obtained. By doing so, the beam passing through the excitation filter 18 can be brought closest to the central beam.

According to the microscope of the first aspect, the imaging lens 12 is constructed with the imaging optical system provided with the zoom optical system so that the light beam from the specimen 17 is nearly afocal at the pupil position P12 conjugate with the pupil position P11 of the objective lens 11, and thus even when the optical path is elongated, the marginal beam can be prevented from separating extremely from the center. Hence, it becomes easy to obviate the eclipse of the marginal beam. Moreover, since the zoom optical system is used, various observation magnifications can be accommodated.

According to the microscope of the first aspect, the following condition is satisfied:

$$0.6 \leq |\beta| \leq 1.5$$

where $\beta$ is the pupil relay magnification of the relay optical system 20 from the pupil position P11 of the objective lens 11 to the pupil conjugate position P12. Hence, it is avoidable that the eclipse of the marginal light due to the barrier filter 19 becomes liable to occur. It is also avoidable that the angle of incidence of light emerging from the relay optical system on the barrier filter 19 increases significantly and a spectral property is impaired by undergoing the influence of the dependence of the barrier filter 19 on the angle of incidence.

According to the microscope of the first aspect, since the objective optical system 11, the imaging optical system 12, and the relay optical system 20 are constructed to be nearly telecentric optical systems on the surface of the object, at the position of the intermediate image, and on the surface of the image sensor, respectively, angles of rays from the center to the periphery are equalized and the phenomenon of shading inherent in the image sensor is suppressed so that the uniformity of the amount of light can be ensured.

According to the microscope of the first aspect, provision is made so that a fly-eye lens (omitted from the figure) can be placed at the pupil position P13 conjugate with the pupil position P11 of the objective lens 11 in the reflecting fluorescence illumination optical system 16. By placing the fly-eye lens (omitted from the figure), the wavelength and amount of illumination light can be further uniformed. By such an arrangement, a Köhler illumination system which does not depend on the light-distribution angle characteristic or the luminance distribution characteristic of the light source can be constructed, and the reflecting fluorescence illumination optical system 16 in which uneven illumination on the surface of the specimen is made more uniform and the dependence of the illumination light source 14 on the light-distribution angle is slight can be constructed.

According to the microscope of the first aspect, the illumination light source 14 is constructed with the reflector light source and hence the amount of light of the illumination light source 14 can be effectively utilized. Also, when the LED light source is used as the illumination light source 14, a long-time observation does not cause damage to an observation object, and a preset wavelength can be used for irradiation in accordance with the application.

According to the microscope of the first aspect, when the microscope is constructed to have an integrator rod (omitted from the figure) in the reflecting fluorescence illumination optical system 16, light from the illumination light source 14 can be uniformed. The integrator rod is constructed in the shape of a square-column glass rod so that light incident on the integrator rod from the light source repeats total reflection in turn and thereby is mixed and illumination distribution is uniformed. By providing critical illumination that the exit end face of the integrator rod is projected on the surface of the specimen, light from the illumination light source 14 can be uniformed. It is further desirable that the integrator rod is constructed so that its square-column shape is similar to the image pickup area. In addition to the glass rod shape, the integrator rod may be constructed with a light pipe in which the square column is hollow and is constructed with a mirror.

According to the microscope of the first aspect, as shown in FIG. 17, since a pupil modulation means is placed to be movable in and out of the optical path in the proximity of the pupil position P12 conjugate with the pupil position P11 of the objective lens 11, formed between the relay optical system 20 and the imaging lens 12, observations based on various observation techniques can be carried out over the entire image pickup surface with a simple operation and with a high degree of accuracy. For example, when a variable stop VS is placed, as the pupil modulation means, in the proximity of the pupil position P12, the depth of focus of the specimen 17 can be adjusted, and for example, even though a number of sample vessels arranged have individual variations in thickness, the diameter of the variable stop VS is adjusted and thereby a specimen image at an image quality level that the focus is stable can be obtained. As another effect, with respect to the loss of the amount of light due to vignetting inherent in the objective lens in other observation techniques as well as in the fluorescence observation, the aperture stop is adjusted and thereby, although an effective numerical aperture becomes smaller than the numerical aperture of the objective lens, the loss of the amount of marginal light due to the objective lens 11 is eliminated and the amounts of central and marginal light can be equalized.

For example, in the case where the pupil modulation means is constructed with a phase plate PP in which a phase film is zonally provided, the condenser lens 24 of the transmitting illumination optical system 22 is provided with a ring-shaped slit to function as a condenser for phase contrast microscopy, so that the specimen 17 can be irradiated with zonal illumination light corresponding to the phase plate. Whereby, a high-precision phase contrast observation in which the amount of light is uniformed can be carried out over the entire image pickup surface.

Further, in the microscope of the first aspect, when the pupil modulation means is constructed with a Nomarski prism NP as another means, a high-precision phase contrast observation in which the amount of light is uniformed can be carried out over the entire image pickup surface.

According to the microscope of the first aspect, an image restriction means for partially blocking illumination light from the reflecting fluorescence illumination optical system 16 is constructed to be locatable in the proximity of the imaging position Q where the intermediate image of the specimen 17 is formed through the relay optical system 20. Hence, for example, when the image restriction means is constructed with a rotatable Nipkow disk (as shown in FIG. 19A), a confocal microscope which is suitable for the physiological reaction observation and morphology observation of the cell can be constructed. When the image restriction means is constructed with a rotatable slit member (as shown in FIG. 19B), only light from a focal plane passes through the slit member and blurred images before and behind the focal plane are cut off by the slit member so that an image in which blurring is eliminated in the entire image pickup area is obtained. In the image restriction means, when an aperture through which illumination light from the reflecting fluorescence illumination optical system 16 can pass is configured into a rectangular shape corresponding to the shape of the image pickup surface of the image sensor 13, as shown in FIG. 19C, irradiation to the specimen 17 can be restricted within a necessary limit and damage to the specimen 17 and fluorescence bleaching can be kept to a minimum.

Further, in the microscope of the first aspect, a deflection member, such as a mirror M1 deflecting the optical path from the objective lens 11 to the imaging lens 12 in a nearly horizontal direction is located at a preset place between the objective lens 11 and the relay optical system 20. In this case, when the microscope is constructed to have an eyepiece optical system for making a visual observation, a vertical length of the microscope can be kept by bending the optical path in the horizontal direction, and hence a viewer is capable of making the observation in a natural position. A split means PR1 splitting the optical path into an optical path to be picked up by the image sensor 13 and an optical path for visual observation is provided at a preset position on the optical path from the objective lens 11 to the imaging lens 12, deflected through the deflection member. Whereby, the microscope in which the image of the specimen 17 picked up can be observed by a display device and in addition, an observation with the naked eye can also be made in a natural position is obtained.

According to the microscope of the first aspect, an autofocus correction mechanism AF is provided between the objective lens 11 and the imaging lens 12, and thereby a sharp observation image is obtained without performing the manual operation of focus adjustment. This is further desirable. In this case, the specimen is illuminated with light of infrared wavelength used for focal position detection, through the objective lens, and the focal position can be detected with high accuracy through a light-receiving element provided in the autofocus correction mechanism by reflected light from the surface or vessel surface of the specimen.

Also, in the microscope shown in FIG. 3, light emanating from the specimen 17 can also be observed without emitting illumination light from the light source 14. In this case as well, the marginal beam can be prevented from separating from the central beam in going from the objective lens 11 to the imaging lens 12 through the relay optical system 20. Consequently, even though the optical path between the objective lens 11 and the imaging lens 12 is elongated, the eclipse of light passing through the peripheries can be eliminated and the problem of the insufficiency of the amount of light imaged on the periphery of the image pickup surface of the image sensor 13 is solved so that the amount of light imaged in the entire image pickup area can be uniformed.

Subsequently, in accordance with the drawings, the embodiments of the present invention will be explained.

Embodiment 1

Figure 4:
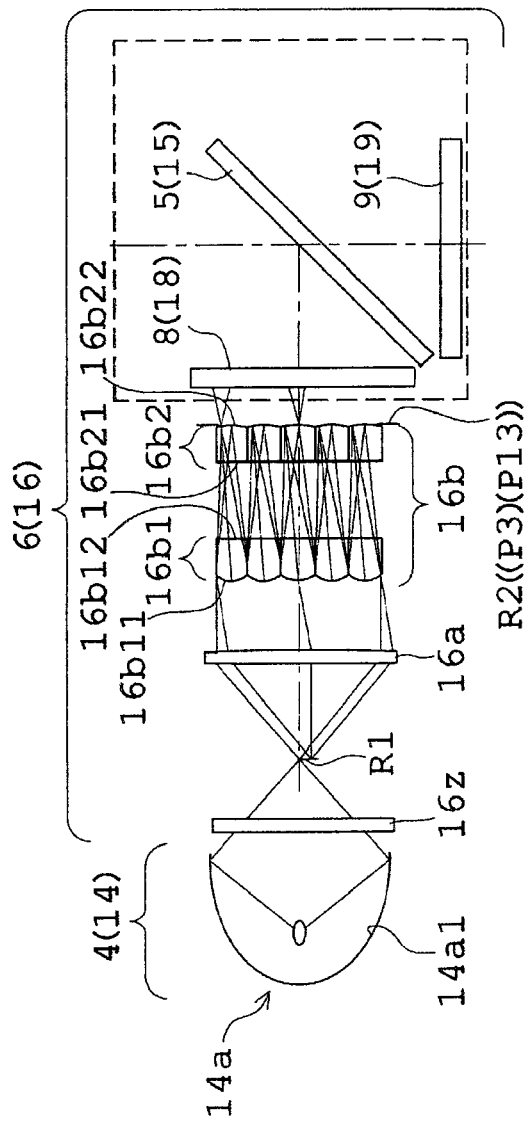
FIG. 4 is an explanatory view showing the arrangement of an illumination light source and a reflecting fluorescence illumination optical system in the microscope according to Embodiment 1 of the present invention.

FIG. 4 is an explanatory view showing the arrangement of an illumination light source and a reflecting fluorescence illumination optical system in the microscope according to Embodiment 1 of the present invention. In the microscope of Embodiment 1, the illumination light source 4 (14) is constructed with a collection-type reflector light source 14a. The reflecting fluorescence illumination optical system 6 (16) includes a collector lens 16a, a fly-eye lens 16b, the excitation filter 8 (18), and the dichroic mirror 5 (15). Also, in FIG. 4, reference numeral 9 (19) represents the barrier filter. The reflector light source 14a is constructed with an arc light source, such as a mercury lamp or a metal halide lamp, provided with an elliptical reflector mirror 14a1. The elliptical reflector mirror 14a1 is constructed so that a convergent beam is emitted by reflection to form a primary light source image at a primary imaging position R1. The collector lens 16a is constructed so that a light beam diverging from the primary imaging position R1 is converted into a parallel beam.

The fly-eye lens 16b includes a first fly-eye lens 16b1 and a second fly-eye lens 16b2. The first fly-eye lens 16b1 is constructed with an array of a plurality of lenses whose entrance end faces 16b11 are each configured to be convex and whose exit end faces 16b12 to be flat. The second fly-eye lens 16b2 is constructed with an array of a plurality of lenses whose entrance end faces 16b21 are each configured to be flat and whose exit end faces 16b22 to be convex. The contour of each lens array assumes the shape of a hexagon or a rectangle. The second fly-eye lens 16b2 is placed so that the position of the exit end faces 16b22 practically coincides with the pupil position P3 (P13) conjugate with the pupil position of the objective lens (omitted from the figure). The fly-eye lens 16b is such that a parallel beam emerging from the collector lens 16a is split into a plurality of beams to form a plurality of secondary light source images in the reflector light source 14a at a secondary imaging position R2 in the proximity of the exit end faces 16b22 of the second fly-eye lens 16b2. Also, the fly-eye lens 16b may be designed to use a lens array in which convex surfaces are integrally provided on both its entrance end faces and exit end faces.

Between the reflector light source 14a and the primary imaging position R1, an infrared cutoff filter 16z is interposed. Also, it is desirable that the back focal position of the collector lens 16a practically coincides with the position of the entrance end faces of the fly-eye lens 16b (the entrance end faces 16b11 of the first fly-eye lens 16b1). As for the rest, an aperture stop (omitted from the figure) is placed in the proximity of the exit end faces of the fly-eye lens 16b (the exit end faces 16b22 of the second fly-eye lens 16b2).

Between the reflector light source 14a and the excitation filter 8 (18), a shutter section (omitted from the figure) for cutting off the light beam from the reflector light source 14a is provided. The locations and structures of the objective lens (omitted from the figure), the imaging lens (omitted from the figure), the excitation filter 8 (18), the dichroic mirror 5 (15), the barrier filter 9 (19), the relay optical system (omitted from the figure), and other members are almost the same as in the microscope shown in FIG. 2 or the microscope of the first aspect shown in FIG. 3.

In the microscope of Embodiment 1 constructed as mentioned above, the convergent beam emitted from the reflector light source 14a forms the primary light source image at the primary imaging position R1 after the infrared wavelength is removed by the infrared cutoff filter 16z, and changes into a divergent beam from the primary imaging position R1 to enter the collector lens 16a. The divergent beam incident on the collector lens 16a is converted by the collector lens 16a into a parallel beam, which is incident on the first fly-eye lens 16b1. The parallel beam incident on the first fly-eye lens 16b1 is split into a plurality of beams converged through a plurality of entrance end faces 16b11, which are incident on the second fly-eye lens 16b2 and form a plurality of secondary light source images at the secondary imaging position R2 in the proximity of the exit end faces 16b22 of the second fly-eye lens 16b2. The plurality of secondary light source images formed at the secondary imaging position R2 in the proximity of the exit end faces 16b22 of the second fly-eye lens 16b2, as in the microscope shown in FIG. 2 or the microscope of the first aspect shown in FIG. 3, after traveling through the excitation filter 8 (18) and the dichroic mirror 5 (15), are relayed through the relay optical system (omitted from the figure) to form a plurality of light source images of the proximity of the pupil position of the objective lens (omitted from the figure).

According to the microscope of Embodiment 1, the collection-type reflector light source 14a forming the light source image is used as the illumination light source, and hence the optical arrangement of the illumination light source and the reflecting fluorescence illumination optical system can be made compact. Other functions and effects are almost the same as in the microscope shown in FIG. 2 or the microscope of the first aspect shown in FIG. 3.

Embodiment 2

Figure 5:
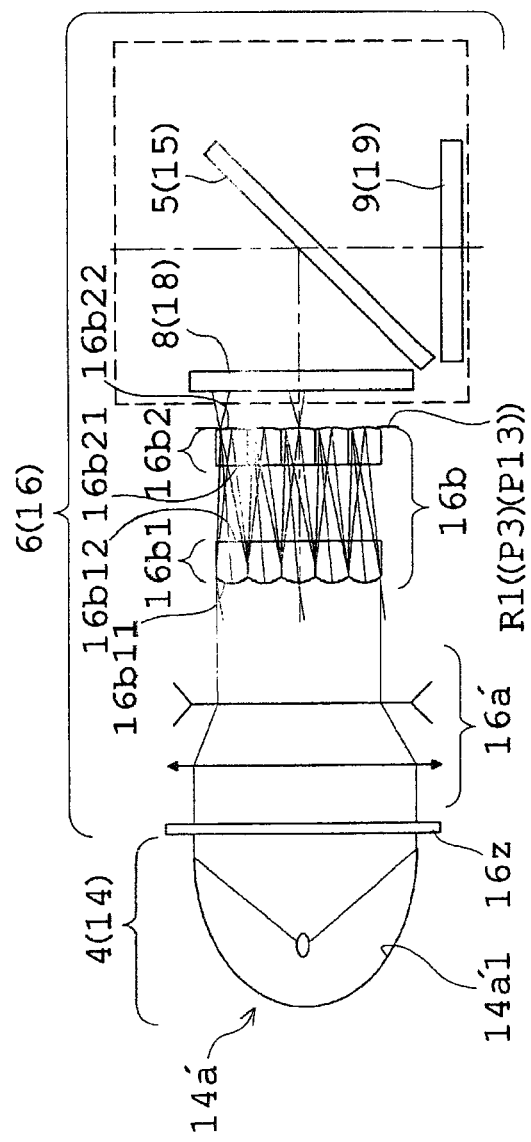
FIG. 5 is an explanatory view showing the arrangement of an illumination light source and a reflecting fluorescence illumination optical system in the microscope according to Embodiment 2 of the present invention.

FIG. 5 is an explanatory view showing the arrangement of an illumination light source and a reflecting fluorescence illumination optical system in the microscope according to Embodiment 2 of the present invention. In the microscope of Embodiment 2, the illumination light source 4 (14) is constructed with a parallel-beam-type reflector light source 14a'. The reflecting fluorescence illumination optical system 6 (16) includes an afocal system 16a', the fly-eye lens 16b, the excitation filter 8 (18), and the dichroic mirror 5 (15). Also, in FIG. 5, reference numeral 9 (19) represents the barrier filter. The reflector light source 14a' is constructed with an arc light source, such as a mercury lamp or a metal halide lamp, provided with an elliptical reflector mirror 14a1'. The elliptical reflector mirror 14a1' is constructed so that a parallel beam is emitted by reflection.

The afocal system 16a' is constructed so that the diameter of the parallel beam emitted from the reflector light source 14a' is converted to become nearly equal to that of the fly-eye lens 16b. The fly-eye lens 16b includes the first fly-eye lens 16b1 and the second fly-eye lens 16b2. The first fly-eye lens 16b1 is constructed with an array of a plurality of lenses whose entrance end faces 16b11 are each configured to be convex and whose exit end faces 16b12 to be flat. The second fly-eye lens 16b2 is constructed with an array of a plurality of lenses whose entrance end faces 16b21 are each configured to be flat and whose exit end faces 16b22 to be convex. The contour of each lens array assumes the shape of a hexagon or a rectangle. The second fly-eye lens 16b2 is placed so that the position of the exit end faces 16b22 practically coincides with the pupil position P3 (P13) conjugate with the pupil position of the objective lens (omitted from the figure). The fly-eye lens 16b is such that a parallel beam emerging from the afocal system 16a' is split into a plurality of beams to form a plurality of primary light source images of the reflector light source 14a' at the primary imaging position R1 in the proximity of the exit end faces 16b22 of the second fly-eye lens 16b2. Also, the fly-eye lens 16b may be designed to use a lens array in which convex surfaces are integrally provided on both its entrance end faces and exit end faces.

Between the reflector light source 14a' and the afocal system 16a', the infrared cutoff filter 16z is interposed. Also, it is desirable that the back focal position of the afocal system 16a' practically coincides with the position of the entrance end faces of the fly-eye lens 16b (the entrance end faces 16b11 of the first fly-eye lens 16b1). As for the rest, the aperture stop (omitted from the figure) is placed in the proximity of the exit end faces of the fly-eye lens 16b (the exit end faces 16b22 of the second fly-eye lens 16b2). Between the reflector light source 14a' and the excitation filter 8 (18), the shutter section (omitted from the figure) for cutting off the light beam from the reflector light source 14a' is provided. The locations and structures of the objective lens (omitted from the figure), the imaging lens (omitted from the figure), the excitation filter 8 (18), the dichroic mirror 5 (15), the barrier filter 9 (19), the relay optical system (omitted from the figure), and other members are almost the same as in the microscope shown in FIG. 2 or the microscope of the first aspect shown in FIG. 3.

In the microscope of Embodiment 2 constructed as mentioned above, the parallel beam emitted from the reflector light source 14a' is incident on the afocal system 16a' after the infrared wavelength is removed by the infrared cutoff filter 16z. The parallel beam incident on the afocal system 16a' is converted so that its beam diameter becomes nearly equal to the diameter of the fly-eye lens 16b, and is incident on the first fly-eye lens 16b1. The parallel beam incident on the first fly-eye lens 16b1 is split into a plurality of beams converged through a plurality of entrance end faces 16b11, which are incident on the second fly-eye lens 16b2 and form a plurality of primary light source images at the primary imaging position R1 in the proximity of the exit end faces 16b22 of the second fly-eye lens 16b2. The plurality of primary light source images formed at the primary imaging position R1 in the proximity of the exit end faces 16b22 of the second fly-eye lens 16b2, as in the microscope shown in FIG. 2 or the microscope of the first aspect shown in FIG. 3, after traveling through the excitation filter 8 (18) and the dichroic mirror 5 (15), are relayed through the relay optical system (omitted from the figure) to form a plurality of light source images of the proximity of the pupil position of the objective lens (omitted from the figure).

According to the microscope of Embodiment 2, the parallel-beam-type reflector light source 14a' emitting the parallel beam is used as the illumination light source, and hence the number of degrees of length freedom in the direction of the optical axis in the optical arrangement of the illumination light source and the reflecting fluorescence illumination optical system becomes large and the number of degrees of placement freedom of constituent members can be increased. Other functions and effects are almost the same as in the microscope shown in FIG. 2 or the microscope of the first aspect shown in FIG. 3.

Embodiment 3

Figure 6:
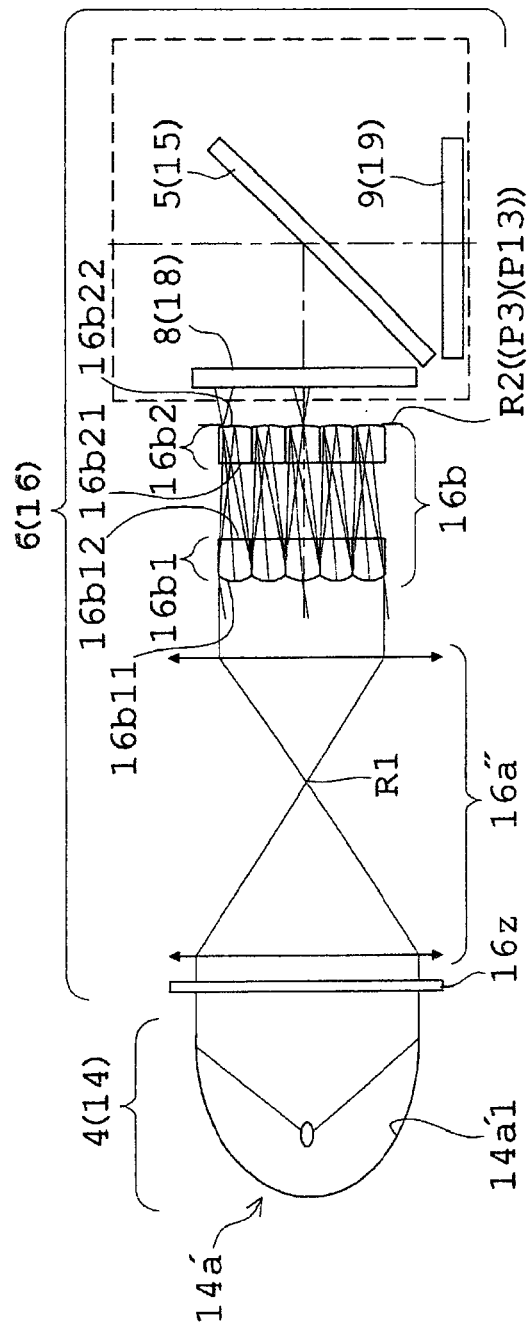
FIG. 6 is an explanatory view showing the arrangement of an illumination light source and a reflecting fluorescence illumination optical system in the microscope according to Embodiment 3 of the present invention.

FIG. 6 is an explanatory view showing the arrangement of an illumination light source and a reflecting fluorescence illumination optical system in the microscope according to Embodiment 3 of the present invention. In the microscope of Embodiment 3, the illumination light source 4 (14) is constructed with the parallel-beam-type reflector light source 14a'. The reflecting fluorescence illumination optical system 6 (16) includes an afocal system 16a'', the fly-eye lens 16b, the excitation filter 8 (18), and the dichroic mirror 5 (15). Also, in FIG. 6, reference numeral 9 (19) represents the barrier filter.

The reflector light source 14a' is constructed with the arc light source, such as a mercury lamp or a metal halide lamp, provided with the elliptical reflector mirror 14a1'. The elliptical reflector mirror 14a1' is constructed so that a parallel beam is emitted by reflection. The afocal system 16a'' is constructed so that the parallel beam emitted from the reflector light source 14a' is condensed to form the light source image of the reflector light source 14a' at the primary imaging position R1 inside the system, and then the beam is converted into a parallel beam whose diameter is nearly equal to that of the fly-eye lens 16b and emerges therefrom.

The fly-eye lens 16b includes the first fly-eye lens 16b1 and the second fly-eye lens 16b2. The first fly-eye lens 16b1 is constructed with an array of a plurality of lenses whose entrance end faces 16b11 are each configured to be convex and whose exit end faces 16b12 to be flat. The second fly-eye lens 16b2 is constructed with an array of a plurality of lenses whose entrance end faces 16b21 are each configured to be flat and whose exit end faces 16b22 to be convex. The contour of each lens array assumes the shape of a hexagon or a rectangle. The second fly-eye lens 16b2 is placed so that the position of the exit end faces 16b22 practically coincides with the pupil position P3 (P13) conjugate with the pupil position of the objective lens (omitted from the figure). The fly-eye lens 16b is such that the parallel beam emerging from the afocal system 16a'' is split into a plurality of beams to form a plurality of secondary light source images of the reflector light source 14a' at the secondary imaging position R2 in the proximity of the exit end faces 16b22 of the second fly-eye lens 16b2. Also, the fly-eye lens 16b may be designed to use a lens array in which convex surfaces are integrally provided on both its entrance end faces and exit end faces.

Between the reflector light source 14a' and the afocal system 16a'', the infrared cutoff filter 16z is interposed. Also, it is desirable that the back focal position of the afocal system 16a'' practically coincides with the position of the entrance end faces of the fly-eye lens 16b (the entrance end faces 16b11 of the first fly-eye lens 16b1). As for the rest, the aperture stop (omitted from the figure) is placed in the proximity of the exit end faces of the fly-eye lens 16b (the exit end faces 16b22 of the second fly-eye lens 16b2). Between the reflector light source 14a' and the excitation filter 8 (18), the shutter section (omitted from the figure) for cutting off the light beam from the reflector light source 14a' is provided. The locations and structures of the objective lens (omitted from the figure), the imaging lens (omitted from the figure), the excitation filter 8 (18), the dichroic mirror 5 (15), the barrier filter 9 (19), the relay optical system (omitted from the figure), and other members are almost the same as in the microscope shown in FIG. 2 or the microscope of the first aspect shown in FIG. 3.

In the microscope of Embodiment 3 constructed as mentioned above, the parallel beam emitted from the reflector light source 14a' is incident on the afocal system 16a'' after the infrared wavelength is removed by the infrared cutoff filter 16z. The parallel beam incident on the afocal system 16a'' is condensed to form the primary light source image at the primary imaging position R1 inside the system, and then the beam is converted into a parallel beam whose diameter is nearly equal to that of the fly-eye lens 16b, which emerges therefrom to enter the first fly-eye lens 16b1. The parallel beam incident on the first fly-eye lens 16b1 is split into a plurality of beams converged through a plurality of entrance end faces 16b11, which are incident on the second fly-eye lens 16b2 and form a plurality of secondary light source images at the secondary imaging position R2 in the proximity of the exit end faces 16b22 of the second fly-eye lens 16b2. The plurality of secondary light source images formed at the secondary imaging position R2 in the proximity of the exit end faces 16b22 of the second fly-eye lens 16b2, as in the microscope shown in FIG. 2 or the microscope of the first aspect shown in FIG. 3, after traveling through the excitation filter 8 (18) and the dichroic mirror 5 (15), are relayed through the relay optical system (omitted from the figure) to form a plurality of light source images of the proximity of the pupil position of the objective lens (omitted from the figure).

According to the microscope of Embodiment 3, like the microscope of Embodiment 2, the parallel-beam-type reflector light source 14a' emitting a parallel beam is used as the illumination light source, and hence the number of degrees of length freedom in the direction of the optical axis in the optical arrangement of the illumination light source and the reflecting fluorescence illumination optical system becomes large and the number of degrees of placement freedom of constituent members can be increased. Other functions and effects are almost the same as in the microscope shown in FIG. 2 or the microscope of the first aspect shown in FIG. 3.

Embodiment 4

Figure 7:
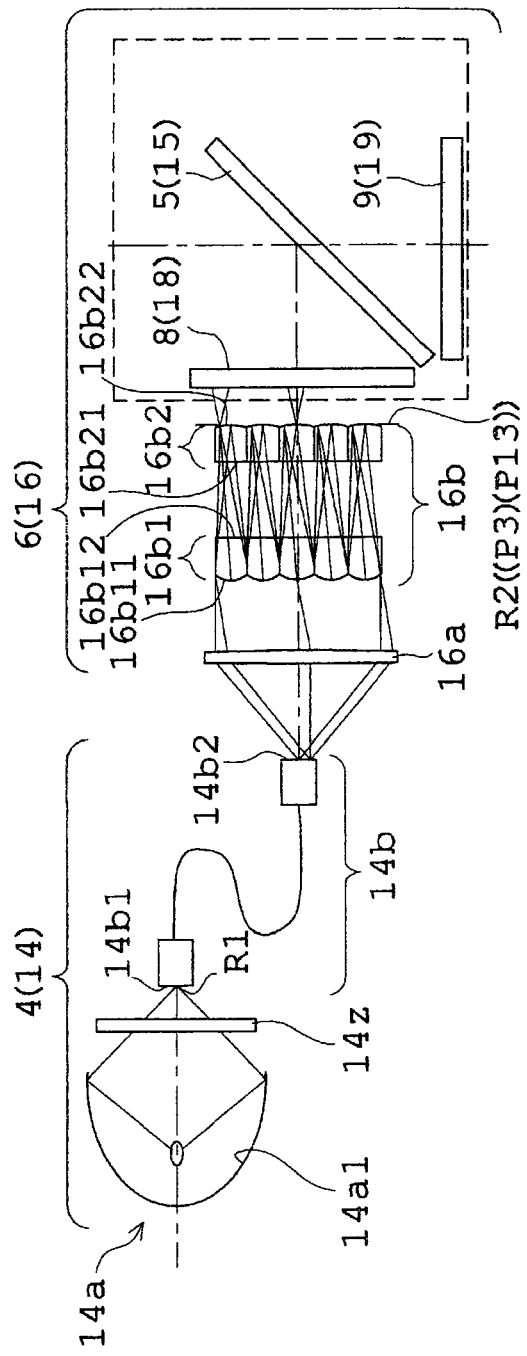
FIG. 7 is an explanatory view showing the arrangement of an illumination light source and a reflecting fluorescence illumination optical system in the microscope according to Embodiment 4 of the present invention.

FIG. 7 is an explanatory view showing the arrangement of an illumination light source and a reflecting fluorescence illumination optical system in the microscope according to Embodiment 4 of the present invention. In the microscope of Embodiment 4, the illumination light source 4 (14) has the collection-type reflector light source 14a and an optical fiber 14b. The reflecting fluorescence illumination optical system 6 (16) includes the collector lens 16a, the fly-eye lens 16b, the excitation filter 8 (18), and the dichroic mirror 5 (15). Also, in FIG. 7, reference numeral 9 (19) represents the barrier filter. The reflector light source 14a is constructed with the arc light source, such as a mercury lamp or a metal halide lamp, provided with the elliptical reflector mirror 14a1. The elliptical reflector mirror 14a1 is constructed so that a convergent beam is emitted by reflection to form the primary light source image at the primary imaging position R1. Also, instead of the collection-type reflector light source 14a, the parallel-beam-type reflector light source may be used so that a lens in which a parallel beam emitted from the parallel-beam-type reflector light source is condensed to perform the primary formation of the light source image of the reflector light source is interposed between the optical fiber 14b s5 and the reflector light source. The illumination light source 4 (14) may be designed to use an LED or a short-arc extra-high voltage mercury lamp as another light source. The optical fiber 14b is placed so that its entrance end face 14b1 is located at the primary imaging position R1 of the light source image of the reflector light source 14a. For the optical fiber 14b, any structural fiber, such as a liquid fiber or a bundle fiber, can be used. Also, it is desirable to use a liquid fiber of high ultraviolet transmittance.

The collector lens 16a is constructed so that a divergent beam emerging from an exit end face 14b2 of the optical fiber 14b is converted into a parallel beam. The fly-eye lens 16b includes the first fly-eye lens 16b1 and the second fly-eye lens 16b2. The first fly-eye lens 16b1 is constructed with an array of a plurality of lenses whose entrance end faces 16b11 are each configured to be convex and whose exit end faces 16b12 to be flat. The second fly-eye lens 16b2 is constructed with an array of a plurality of lenses whose entrance end faces 16b21 are each configured to be flat and whose exit end faces 16b22 to be convex. The contour of each lens array assumes the shape of a hexagon or a rectangle. The second fly-eye lens 16b2 is placed so that the position of the exit end faces 16b22 practically coincides with the pupil position P3 (P13) conjugate with the pupil position of the objective lens (omitted from the figure). The fly-eye lens 16b is such that a parallel beam emerging from the collector lens 16a is split into a plurality of beams to form a plurality of secondary light source images of the reflector light source 14a at the secondary imaging position R2 in the proximity of the exit end faces 16b22 of the second fly-eye lens 16b2. Also, the fly-eye lens 16b may be designed to use a lens array in which convex surfaces are integrally provided on both its entrance end faces and exit end faces.

Between the reflector light source 14a and the optical fiber 14b, an infrared cutoff filter 14z is interposed. Also, it is desirable that the back focal position of the collector lens 16a practically coincides with the position of the entrance end faces of the fly-eye lens 16b (the entrance end faces 16b11 of the first fly-eye lens 16b1). As for the rest, the aperture stop (omitted from the figure) is placed in the proximity of the exit end faces of the fly-eye lens 16b (the exit end faces 16b22 of the second fly-eye lens 16b2). Between the reflector light source 14a and the excitation filter 8 (18), the shutter section (omitted from the figure) for cutting off the light beam from the reflector light source 14a is provided. The locations and structures of the objective lens (omitted from the figure), the imaging lens (omitted from the figure), the excitation filter 8 (18), the dichroic mirror 5 (15), the barrier filter 9 (19), the relay optical system (omitted from the figure), and other members are almost the same as in the microscope shown in FIG. 2 or the microscope of the first aspect shown in FIG. 3.

In the microscope of Embodiment 4 constructed as mentioned above, the convergent beam emitted from the reflector light source 14a forms the primary light source image at the primary imaging position R1 after the infrared wavelength is removed by the infrared cutoff filter 14z, and is incident on the entrance end face 14b1 of the optical fiber 14b. Light incident on the entrance end face 14b1 of the optical fiber 14b emerges as a divergent beam from the exit end face 14b2. The divergent beam emerging from the exit end face 14b2 of the optical fiber 14b is incident on the collector lens 16a. The divergent beam incident on the collector lens 16a is converted by the collector lens 16a into a parallel beam, which is incident on the first fly-eye lens 16b1. The parallel beam incident on the first fly-eye lens 16b1 is split into a plurality of beams converged through a plurality of entrance end faces 16b11, which are incident on the second fly-eye lens 16b2 and form a plurality of secondary light source images at the secondary imaging position R2 in the proximity of the exit end faces 16b22 of the second fly-eye lens 16b2. The plurality of secondary light source images formed at the secondary imaging position R2 in the proximity of the exit end faces 16b22 of the second fly-eye lens 16b2, as in the microscope shown in FIG. 2 or the microscope of the first aspect shown in FIG. 3, after traveling through the excitation filter 8 (18) and the dichroic mirror 5 (15), are relayed through the relay optical system (omitted from the figure) to form a plurality of light source images of the proximity of the pupil position of the objective lens (omitted from the figure).

According to the microscope of Embodiment 4, the optical fiber 14b is placed in the reflecting fluorescence illumination optical system, and hence the number of degrees of kind and placement freedom of the illumination light source can be increased. Other functions and effects are almost the same as in the microscope shown in FIG. 2 or the microscope of the first aspect shown in FIG. 3.

Embodiment 5

Figure 8:
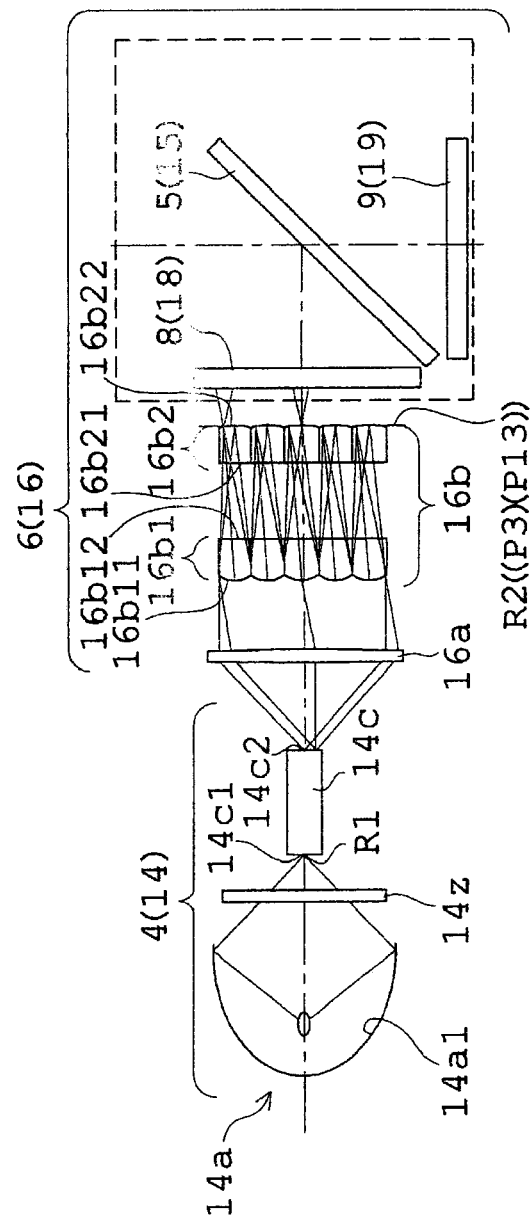
FIG. 8 is an explanatory view showing the arrangement of an illumination light source and a reflecting fluorescence illumination optical system in the microscope according to Embodiment 5 of the present invention.

FIG. 8 is an explanatory view showing the arrangement of an illumination light source and a reflecting fluorescence illumination optical system in the microscope according to Embodiment 5 of the present invention. The microscope of Embodiment 5 is constructed to have an integrator rod 14c instead of the optical fiber 14b in the microscope of Embodiment 4 shown in FIG. 7. The reflector light source 14a is constructed with the arc light source, such as a mercury lamp or a metal halide lamp, provided with the elliptical reflector mirror 14a1. The elliptical reflector mirror 14a1 is constructed so that a convergent beam is emitted by reflection to form the primary light source image at the primary imaging position R1. Also, instead of the collection-type reflector light source 14a, the parallel-beam-type reflector light source may be used so that a lens in which a parallel beam emitted from the parallel-beam-type reflector light source is condensed to perform the primary formation of the light source image of the reflector light source is interposed between the integrator rod 14c and the reflector light source. The illumination light source 4 (14) may be designed to use an LED or a short-arc extra-high voltage mercury lamp as another light source.

The integrator rod 14c is constructed with a columnar member of a square-column glass rod shape made from glass material with high ultraviolet transmittance or a light pipe including a hollow square-column mirror so that light incident on the interior repeats total reflection in turn and thereby is mixed and illumination distribution is equalized. An exit end face 14c2 of the integrator rod 14c serves as the plane of the secondary light source image. Also, the cross section of the integrator rod 14c is configured into a rectangular shape similar to the image pickup area of the image sensor (omitted from the figure). The integrator rod 14c is placed so that its entrance end face 14c1 is located at the primary imaging position R1 of the light source image of the reflector light source 14a. The collector lens 16a is designed so that a divergent beam emerging from the exit end face 14c2 of the integrator rod 14c is converted into a parallel beam. Other features are almost the same as in the microscope of Embodiment 4 shown in FIG. 7.

In the microscope of Embodiment 5 constructed as mentioned above, the convergent beam emitted from the reflector light source 14a forms the primary light source image at the primary imaging position R1 after the infrared wavelength is removed by the infrared cutoff filter 14z, and is incident on the entrance end face 14c1 of the integrator rod 14c. Light incident on the entrance end face 14c1 of the integrator rod 14c is diffusely reflected in the interior and thereby is made uniform in light intensity distribution to emerge as a divergent beam from the exit end face 14c2. The divergent beam emerging from the exit end face 14c2 of the integrator rod 14c is incident on the collector lens 16a. The divergent beam incident on the collector lens 16a is converted by the collector lens 16a into a parallel beam, which is incident on the first fly-eye lens 16b1. The parallel beam incident on the first fly-eye lens 16b1 is split into a plurality of beams converged through a plurality of entrance end faces 16b11, which are incident on the second fly-eye lens 16b2 and form a plurality of secondary light source images at the secondary imaging position R2 in the proximity of the exit end faces 16b22 of the second fly-eye lens 16b2. The plurality of secondary light source images formed at the secondary imaging position R2 in the proximity of the exit end faces 16b22 of the second fly-eye lens 16b2, as in the microscope shown in FIG. 2 or the microscope of the first aspect shown in FIG. 3, after traveling through the excitation filter 8 (18) and the dichroic mirror 5 (15), are relayed through the relay optical system (omitted from the figure) to form a plurality of light source images of the proximity of the pupil position of the objective lens (omitted from the figure).

According to the microscope of Embodiment 5, the reflecting fluorescence illumination optical system is provided with the integrator rod 14c, and hence the uniformity of illumination is further improved by combining the integrator rod 14c with the fly-eye lens 16b. Also, in general, when the integrator rod is used, unevenness of a light intensity due to angles of emergent rays is produced, but in the microscope of Embodiment 5, the unevenness of the light intensity is eliminated by the fly-eye lens 16b and the light intensity can be equalized. Other functions and effects are almost the same as in the microscope shown in FIG. 2 or the microscope of the first aspect shown in FIG. 3.

Embodiment 6

Figure 9:
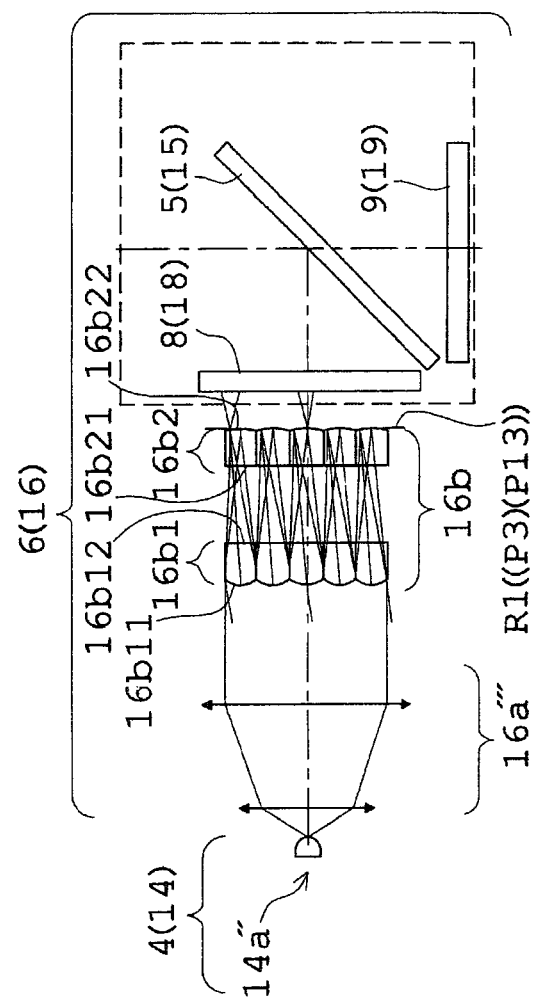
FIG. 9 is an explanatory view showing the arrangement of an illumination light source and a reflecting fluorescence illumination optical system in the microscope according to Embodiment 6 of the present invention.

FIG. 9 is an explanatory view showing the arrangement of an illumination light source and a reflecting fluorescence illumination optical system in the microscope according to Embodiment 6 of the present invention. In the microscope of Embodiment 6, the illumination light source 4 (14) is constructed with an LED light source 14a". The reflecting fluorescence illumination optical system 6 (16) includes a collector lens 16a''', the fly-eye lens 16b, the excitation filter 8 (18), and the dichroic mirror 5 (15). Also, in FIG. 9, reference numeral 9 (19) denotes the barrier filter. The collector lens 16a''' is designed so that a divergent beam emitted from the LED light source 14a" is converted into a parallel beam.

The fly-eye lens 16b includes the first fly-eye lens 16b1 and the second fly-eye lens 16b2. The first fly-eye lens 16b1 is constructed with an array of a plurality of lenses whose entrance end faces 16b11 are each configured to be convex and whose exit end faces 16b12 to be flat. The second fly-eye lens 16b2 is constructed with an array of a plurality of lenses whose entrance end faces 16b21 are each configured to be flat and whose exit end faces 16b22 to be convex. The contour of each lens array assumes the shape of a hexagon or a rectangle. The second fly-eye lens 16b2 is placed so that the position of the exit end faces 16b22 practically coincides with the pupil position P3 (P13) conjugate with the pupil position of the objective lens (omitted from the figure). The fly-eye lens 16b is such that the parallel beam emerging from the collector lens 16a''' is split into a plurality of beams to form a plurality of primary light source images of the LED light source 14a" at the primary imaging position R1 in the proximity of the exit end faces 16b22 of the second fly-eye lens 16b2. Also, the fly-eye lens 16b may be designed to use a lens array in which convex surfaces are integrally provided on both its entrance end faces and exit end faces.

Also, it is desirable that the back focal position of the collector lens 16a''' practically coincides with the position of the entrance end faces of the fly-eye lens 16b (the entrance end faces 16b1 of the first fly-eye lens 16b1). As for the rest, the aperture stop (omitted from the figure) is placed in the proximity of the exit end faces of the fly-eye lens 16b (the exit end faces 16b22 of the second fly-eye lens 16b2). Between the LED light source 14a" and the excitation filter 8 (18), the shutter section (omitted from the figure) for cutting off the light beam from the LED light source 14a" is provided. The locations and structures of the objective lens (omitted from the figure), the imaging lens (omitted from the figure), the excitation filter 8 (18), the dichroic mirror 5 (15), the barrier filter 9 (19), the relay optical system (omitted from the figure), and other members are almost the same as in the microscope shown in FIG. 2 or the microscope of the first aspect shown in FIG. 3.

In the microscope of Embodiment 6 constructed as mentioned above, the convergent beam emitted from the LED light source 14a" is incident on the collector lens 16a'''. The divergent beam incident on the collector lens 16a''' is converted by the collector lens 16a''' into a parallel beam, which is incident on the first fly-eye lens 16b1. The parallel beam incident on the first fly-eye lens 16b1 is split into a plurality of beams converged through a plurality of entrance end faces 16b11, which are incident on the second fly-eye lens 16b2 and form a plurality of primary light source images at the primary imaging position R1 in the proximity of the exit end faces 16b22 of the second fly-eye lens 16b2. The plurality of primary light source images formed at the primary imaging position R1 in the proximity of the exit end faces 16b22 of the second fly-eye lens 16b2, as in the microscope shown in FIG. 2 or the microscope of the first aspect shown in FIG. 3, after traveling through the excitation filter 8 (18) and the dichroic mirror 5 (15), are relayed through the relay optical system (omitted from the figure) to form a plurality of light source images of the proximity of the pupil position of the objective lens (omitted from the figure).

According to the microscope of Embodiment 6, the LED light source 14a" is used as the illumination light source, and therefore, unlike the arc light source such as the reflector light source, brightness can be electrically controlled. Consequently, the brightness can be switched with a high speed in accordance with the observation application. Moreover, since the brightness can be kept in a constant state, observation accuracy is improved in the case where the specimen is illuminated for a long period of time and a change with age of the specimen is observed. Other functions and effects are almost the same as in the microscope shown in FIG. 2 or the microscope of the first aspect shown in FIG. 3.

Embodiment 7

Figure 10:
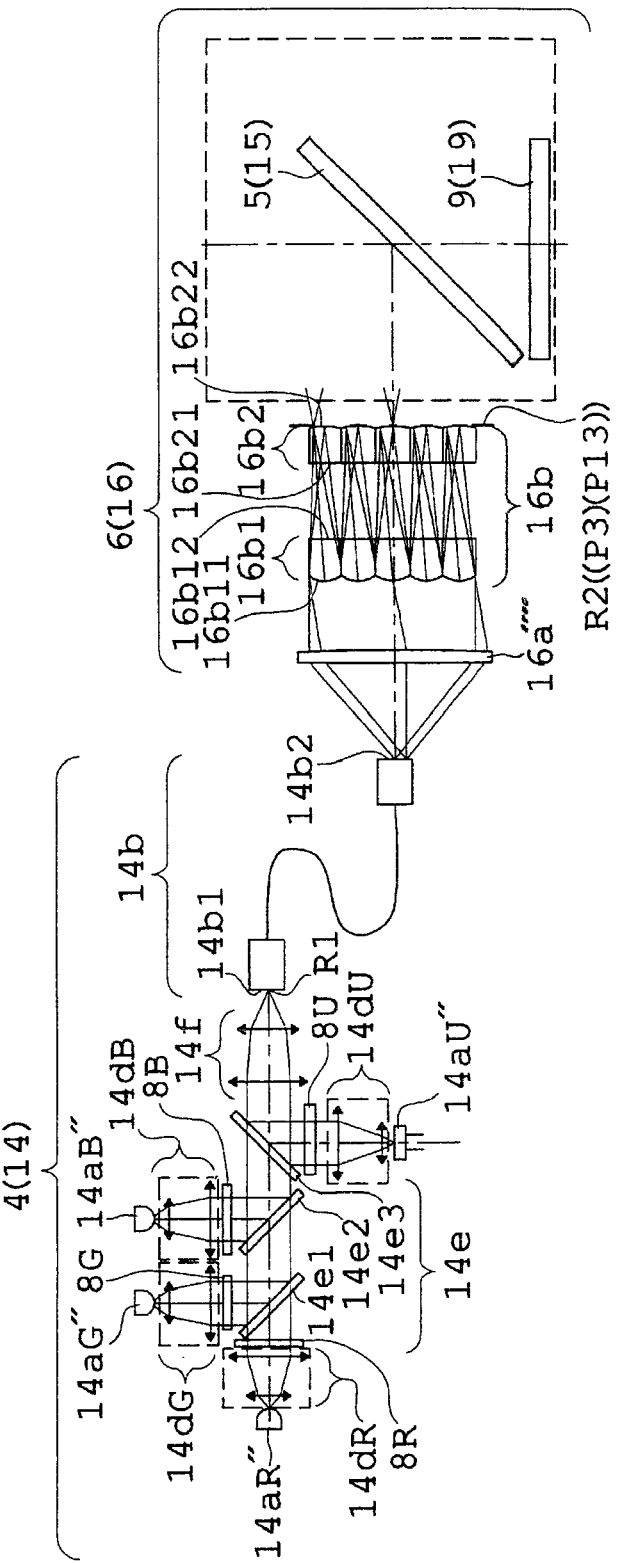
FIG. 10 is an explanatory view showing the arrangement of an illumination light source and a reflecting fluorescence illumination optical system in the microscope according to Embodiment 7 of the present invention.

FIG. 10 is an explanatory view showing the arrangement of an illumination light source and a reflecting fluorescence illumination optical system in the microscope according to Embodiment 7 of the present invention. In the microscope of Embodiment 7, the illumination light source 4 (14) has a red LED light source 14$a$R"; a green LED light source 14$a$G"; a blue LED light source 14$a$B"; an ultraviolet LED light source 14$a$U"; first collector lenses 14$d$R, 14$d$G, 14$d$B, and 14$d$U; a path combining means 14$e$; a light-condensing optical system 14$f$; and the optical fiber 14$b$. The reflecting fluorescence illumination optical system 6 (16) includes a second collector lens 16$a$"", the fly-eye lens 16$b$, and the dichroic mirror 5 (15). Also, in FIG. 10, reference numeral 9 (19) denotes the barrier filter. The first collector lenses 14$d$R, 14$d$G, 14$d$B, and 14$d$U are provided to correspond to the LED light sources 14$a$R", 14$a$G", 14$a$B", 14$a$U", respectively, so that divergent beams emitted from individual LED light sources are converted into parallel beams, which emerge therefrom.

The path combining means 14$e$ includes a dichroic mirror 14$e$1, a dichroic mirror 14$e$2, and a dichroic mirror 14$e$3. The dichroic mirror 14$e$1 has the property of transmitting infrared light and reflecting green light, and is placed at a position where the optical path of the parallel beam of red color emerging from the first collector lens 14$d$R intersects the optical path of the parallel beam of green color emerging from the first collector lens 14$d$G. The dichroic mirror 14$e$2 has the property of transmitting infrared and green light and reflecting blue light, and is placed at a position where the optical path of a parallel beam combined through the dichroic mirror 14$e$1 intersects the optical path of the parallel beam of blue color emerging from the first collector lens 14$d$B. The dichroic mirror 14$e$3 has the property of transmitting red, green, and blue light and reflecting ultraviolet light, and is placed at a position where the optical path of a parallel beam combined through the dichroic mirrors 14$e$1 and 14$e$2 intersects the optical path of the parallel beam of ultraviolet color emerging from the first collector lens 14$d$U.

The light-condensing optical system 14$f$ is constructed so that a parallel beam combined through the path combining means 14$e$ is condensed and light source images of individual LED light sources are formed at the primary imaging position R1. The optical fiber 14$b$ is placed so that its entrance end face 14$b$1 is located at the primary imaging position R1 of the light source image of the reflector light source 14$a$. For the optical fiber 14$b$, any structural fiber, such as a liquid fiber or a bundle fiber, can be used. Also, it is desirable to use a liquid fiber of high ultraviolet transmittance. The second collector lens 16$a$"" is constructed so that a divergent beam emerging from the exit end face 14$b$2 of the optical fiber 14$b$ is converted into a parallel beam.

The fly-eye lens 16$b$ includes the first fly-eye lens 16$b$1 and the second fly-eye lens 16$b$2. The first fly-eye lens 16$b$1 is constructed with an array of a plurality of lenses whose entrance end faces 16$b$11 are each configured to be convex and whose exit end faces 16$b$12 to be flat. The second fly-eye lens 16$b$2 is constructed with an array of a plurality of lenses whose entrance end faces 16$b$21 are each configured to be flat and whose exit end faces 16$b$22 to be convex. The contour of each lens array assumes the shape of a hexagon or a rectangle. The second fly-eye lens 16$b$2 is placed so that the position of the exit end faces 16$b$22 practically coincides with the pupil position P3 (P13) conjugate with the pupil position of the objective lens (omitted from the figure). The fly-eye lens 16$b$ is such that the parallel beam emerging from the second collector lens 16$a$"" is split into a plurality of beams to form a plurality of secondary light source images of the LED light sources 14$a$R", 14$a$G", 14$a$B"$_3$ and 14$a$U" at the secondary imaging position R2 in the proximity of the exit end faces 16$b$22 of the second fly-eye lens 16$b$2. Also, the fly-eye lens 16$b$ may be designed to use a lens array in which convex surfaces are integrally provided on both its entrance end faces and exit end faces.

In the microscope of Embodiment 7, excitation filters 8R, 8G, 8B, and 8U are used instead of the excitation filter 8 (18). The excitation filter 8R has the property of transmitting only red light as excitation light and is interposed between the first collector lens 14$d$R and the dichroic mirror 14$e$1. The excitation filter 8G has the property of transmitting only green light as excitation light and is interposed between the first collector lens 14$d$G and the dichroic mirror 14$e$1. The excitation filter 8B has the property of transmitting only blue light as excitation light and is interposed between the first collector lens 14$d$B and the dichroic mirror 14$e$2. The excitation filter 81J has the property of transmitting only ultraviolet light as excitation light and is interposed between the first collector lens 14$d$U and the dichroic mirror 14$e$3.

Also, it is desirable that the back focal position of the collector lens 16$a$"" practically coincides with the position of the entrance end faces of the fly-eye lens 16$b$ (the entrance end faces 16$b$11 of the first fly-eye lens 16$b$1). As for the rest, the aperture stop (omitted from the figure) is placed in the proximity of the exit end faces of the fly-eye lens 16$b$ (the exit end faces 16$b$22 of the second fly-eye lens 16$b$2). In the range from the LED light source 14$a$R", 14$a$G", 14$a$B", and 14$a$U" to the dichroic mirror 5 (15), the shutter section (omitted from the figure) for cutting off the light beams from the LED light sources 14$a$R", 14$a$G", 14$a$B", and 14$a$U" is provided. The locations and structures of the objective lens (omitted from the figure), the imaging lens (omitted from the figure), the dichroic mirror 5 (15), the barrier filter 9 (19), the relay optical system (omitted from the figure), and other members are almost the same as in the microscope shown in FIG. 2 or the microscope of the first aspect shown in FIG. 3.

In the microscope of Embodiment 7 constructed as mentioned above, the divergent beams emitted from the LED light source 14$a$R", 14$a$G", 14$a$B", and 14$a$U" are incident on the first collector lenses 14$d$R, 14$d$G, 14$d$B, and 14$d$U, respectively, and are converted into parallel beams through the first collector lenses 14$d$R, 14$d$G, 14$d$B, and 14$d$U. Individual parallel beams thus converted are superposed on a common illumination optical axis through the dichroic mirrors 14$e$1, 14$e$2, and 14$e$3. Superposed parallel beams are condensed through the light-condensing optical system 14$f$ to form the primary light source image at the primary imaging position R1 and is incident on the entrance end face 14$b$1 of the optical fiber 14$b$. Light incident on the entrance end face 14$b$1 of the optical fiber 14$b$ emerges as a divergent beam from the exit end face 14$b$2. The divergent beam emerging from the exit end face 14$b$2 of the optical fiber 14$b$ is incident on the second collector lens 16$a$"". The divergent beam incident on the second collector lens 16$a$"" is converted by the second collector lens 16$a$"" into a parallel beam, which is incident on the first fly-eye lens 16$b$1. The parallel beam incident on the first fly-eye lens 16*b*1 is split into a plurality of beams converged through a plurality of entrance end faces 16*b*11, which are incident on the second fly-eye lens 16*b*2 and form a plurality of secondary light source images at the secondary imaging position R2 in the proximity of the exit end faces 16*b*22 of the second fly-eye lens 16*b*2. The plurality of secondary light source images formed at the secondary imaging position R2 in the proximity of the exit end faces 16*b*22 of the second fly-eye lens 16*b*2, as in the microscope shown in FIG. 2 or the microscope of the first aspect shown in FIG. 3, after traveling through the dichroic mirror 5 (15), are relayed through the relay optical system (omitted from the figure) to form a plurality of light source images of the proximity of the pupil position of the objective lens (omitted from the figure). According to the microscope of Embodiment 7, the fluorescence observation with a plurality of wavelengths can be facilitated. Other functions and effects are almost the same as in the microscope of Embodiment 6 shown in FIG. 9.

Embodiment 8

Figure 11:
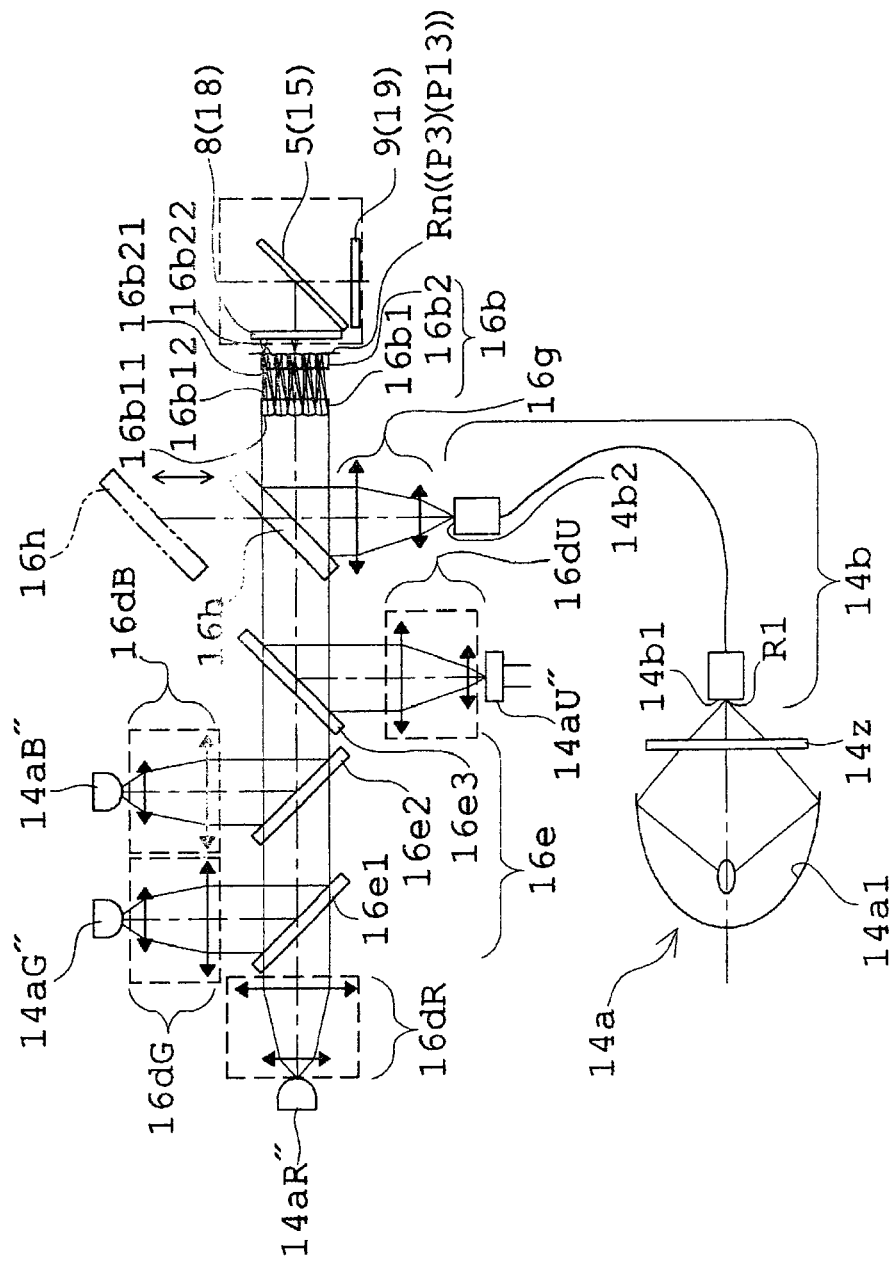
FIG. 11 is an explanatory view showing the arrangement of an illumination light source and a reflecting fluorescence illumination optical system in the microscope according to Embodiment 8 of the present invention.

FIG. 11 is an explanatory view showing the arrangement of an illumination light source and a reflecting fluorescence illumination optical system in the microscope according to Embodiment 8 of the present invention. In the microscope of Embodiment 8, the illumination light source 4 (14) has the red LED light source 14*a*R", the green LED light source 14*a*G", the blue LED light source 14*a*B", the ultraviolet LED light source 14*a*U", the collection-type reflector light source 14*a*, and the optical fiber 14*b*. The reflecting fluorescence illumination optical system 6 (16) includes LED emitted beam converting collector lenses 16*d*R, 16*d*G, 16*d*B, and 16*d*U; a path combining means 16*e*; a fiber emergent beam converting collector lens 16*g*; a mirror 16*h*; the fly-eye lens 16*b*; the excitation filter 8 (18); and the dichroic mirror 5 (15). Also, in FIG. 11, reference numeral 9 (19) denotes the barrier filter.

The reflector light source 14*a* is constructed with the arc light source, such as a mercury lamp or a metal halide lamp, provided with the elliptical reflector mirror 14*a*1. The elliptical reflector mirror 14*a*1 is constructed so that a convergent beam is emitted by reflection to form the primary light source image at the primary imaging position R1. Also, instead of the collection-type reflector light source 14*a*, the parallel-beam-type reflector light source may be used so that a lens in which a parallel beam emitted from the parallel-beam-type reflector light source is condensed to perform the primary formation of the light source image of the reflector light source is interposed between the optical fiber 14*b* and the reflector light source.

The arrangement of the LED emitted beam converting collector lenses 16*d*R, 16*d*G, 16*d*B, and 16*d*U and the path combining means 16*e* is nearly the same as that of the first collector lenses 14*d*R, 14*d*G, 14*d*B, and 14*d*U and the path combining means 14*e* in Embodiment 7 shown in FIG. 10. The fiber emergent beam converting collector lens 16*g* is constructed so that a convergent beam emerging from the exit end face 14*b*2 of the optical fiber 14*b* is converted into a parallel beam, which emerges therefrom. The mirror 16*h* is placed on the optical axis of the path combining means 16*e* to be movable in and out of a common optical axis between a dichroic mirror 16*e*3 and the fly-eye lens 16*b*, and is constructed so that when it is inserted in the optical path, the parallel beam emerging from the fiber emergent beam converting collector lens 16*g* is reflected to enter the fly-eye lens 16*b*.

The fly-eye lens 16*b* includes the first fly-eye lens 16*b*1 and the second fly-eye lens 16*b*2. The first fly-eye lens 16*b*1 is constructed with an array of a plurality of lenses whose entrance end faces 16*b*11 are each configured to be convex and whose exit end faces 16*b*12 to be flat. The second fly-eye lens 16*b*2 is constructed with an array of a plurality of lenses whose entrance end faces 16*b*21 are each configured to be flat and whose exit end faces 16*b*22 to be convex. The contour of each lens array assumes the shape of a hexagon or a rectangle. The second fly-eye lens 16*b*2 is placed so that the position of the exit end faces 16*b*22 practically coincides with the pupil position P3 (P13) conjugate with the pupil position of the objective lens (omitted from the figure). The fly-eye lens 16*b* is such that a parallel beam emerging from the second collector lens 16*g* is split into a plurality of beams to form a plurality of primary light source images or a plurality of secondary light source images of the reflecting light source 14*a* at the exit end faces 16*b*22 of the second fly-eye lens 16*b*2. Also, the fly-eye lens 16*b* may be designed to use a lens array in which convex surfaces are integrally provided on both its entrance end faces and exit end faces. Between the reflector light source 14*a* and the optical fiber 14*b*, the infrared cutoff filter 14*z* is interposed.

Also, it is desirable that the back focal position of the LED emitted beam converting collector lenses 16*d*R, 16*d*G, 16*d*B, and 16*d*U and the fiber emergent beam converting collector lens 16*g* practically coincides with the position of the entrance end faces of the fly-eye lens 16*b* (the entrance end faces 16*b*1 of the first fly-eye lens 16*b*1). As for the rest, an aperture stop (omitted from the figure) is placed in the proximity of the exit end faces of the fly-eye lens 16*b* (the exit end faces 16*b*22 of the second fly-eye lens 16*b*2). In the range from the LED light sources 14*a*R", 14*a*G", 14*a*B", and 14*a*U", and the reflector light source 14*a* to the excitation filter 8 (18), the shutter section (omitted from the figure) for cutting off light beams from the LED light sources 14*a*R", 14*a*G", 14*a*B", and 14*a*U", and the reflector light source 14*a*.

The locations and structures of the objective lens (omitted from the figure), the imaging lens (omitted from the figure), the excitation filter 8 (18), the dichroic mirror 5 (15), the barrier filter 9 (19), the relay optical system (omitted from the figure), and other members are almost the same as in the microscope shown in FIG. 2 or the microscope of the first aspect shown in FIG. 3.

In the microscope of Embodiment 8 constructed as mentioned above, the divergent beams emitted from the LED light source 14*a*R", 14*a*G", 14*a*B", and 14*a*U" are incident on the LED emitted beam converting collector lenses 16*d*R, 16*d*G, 16*d*B, and 16*d*U, respectively, and are converted into parallel beams through the LED emitted beam converting collector lenses 16*d*R, 16*d*G, 16*d*B, and 16*d*U. Individual parallel beams thus converted are superposed on a common illumination optical axis through dichroic mirrors 16*e*1, 16*e*2, and 16*e*3.

On the other hand, the convergent beam emitted from the reflector light source 14*a* forms the primary light source image at the primary imaging position R1 after the infrared wavelength is removed by the infrared cutoff filter 14*z*, and is incident on the entrance end face 14*b*1 of the optical fiber 14*b*. Light incident on the entrance end face 14*b*1 of the optical fiber 14*b* emerges as a divergent beam from the exit end face 14*b*2. The divergent beam emerging from the exit end face 14*b*2 of the optical fiber 14*b* is incident on the fiber emergent beam converting collector lens 16*g*. The divergent beam incident on the fiber emergent beam converting collector lens 16*g* is converted into a parallel beam by the fiber emergent beam converting collector lens 16*g*.

Here, when the mirror 16*h* on the optical path of the path combining means 16*e* is removed from the common optical axis between the dichroic mirror 16e3 and the fly-eye lens 16b, the parallel beams from the LED light source 14aR", 14aG", 14aB", and 14aU" superposed on the common illumination optical axis through the dichroic mirrors 16e1, 16e2, and 16e3 are incident on the first fly-eye lens 16b1. The parallel beams incident on the first fly-eye lens 16b1 are split into a plurality of beams converged through a plurality of entrance end faces 16b11, which are incident on the second fly-eye lens 16b2 and form a plurality of primary light source images of the LED light source 14aR", 14aG", 14aB", and 14aU" at an imaging position Rn in the proximity of the exit end faces 16b22 of the second fly-eye lens 16b2.

On the other hand, when the mirror 16h on the optical path of the path combining means 16e is inserted in the common optical axis between the dichroic mirror 16e3 and the fly-eye lens 16b, the parallel beam from the reflector light source 14a is incident on the first fly-eye lens 16b1. The parallel beam incident on the first fly-eye lens 16b1 is split into a plurality of beams converged through a plurality of the entrance end faces 16b1, which are incident on the second fly-eye lens 16b2 and form a plurality of secondary light source images of the reflector light source 14a at the imaging position Rn in the proximity of the exit end faces 16b22 of the second fly-eye lens 16b2. The plurality of light source images formed at the imaging position Rn in the proximity of the exit end faces 16b22 of the second fly-eye lens 16b2, as in the microscope shown in FIG. 2 or the microscope of the first aspect shown in FIG. 3, after traveling through the excitation filter 8 (18) and the dichroic mirror 5 (15), are relayed through the relay optical system (omitted from the figure) to form a plurality of light source images of the proximity of the pupil position of the objective lens (omitted from the figure).

According to the microscope of Embodiment 8, since the LED light source 14aR", 14aG", 14aB", and 14aU" and the reflector light source 14a are provided so that the parallel beam from either one of the light sources is switched through the mirror 16h to enter the fly-eye lens 16b, the advantages of both the LED light source and the arc light source such as the reflector light source are obtained and the observation application is widened. Specifically, when the LED light source 14aR", 14aG", 14aB", and 14aU" are used, brightness can be electrically controlled and can be switched with a high speed in accordance with the observation application. Moreover, since the brightness can be kept in a constant state, observation accuracy is improved in the case where the specimen is illuminated for a long period of time and a change with age of the specimen is observed. On the other hand, when the reflector light source 14a is used, the fluorescence observation with excitation wavelength which cannot be covered by the LED light source becomes possible because its emergent light is white light. In addition, when the amount of illumination light is insufficient with the LED light source, observations with strong illumination light can be carried out. Other functions and effects are almost the same as in the microscope shown in FIG. 2 or the microscope of the first aspect shown in FIG. 3.

Embodiment 9

Figure 12:
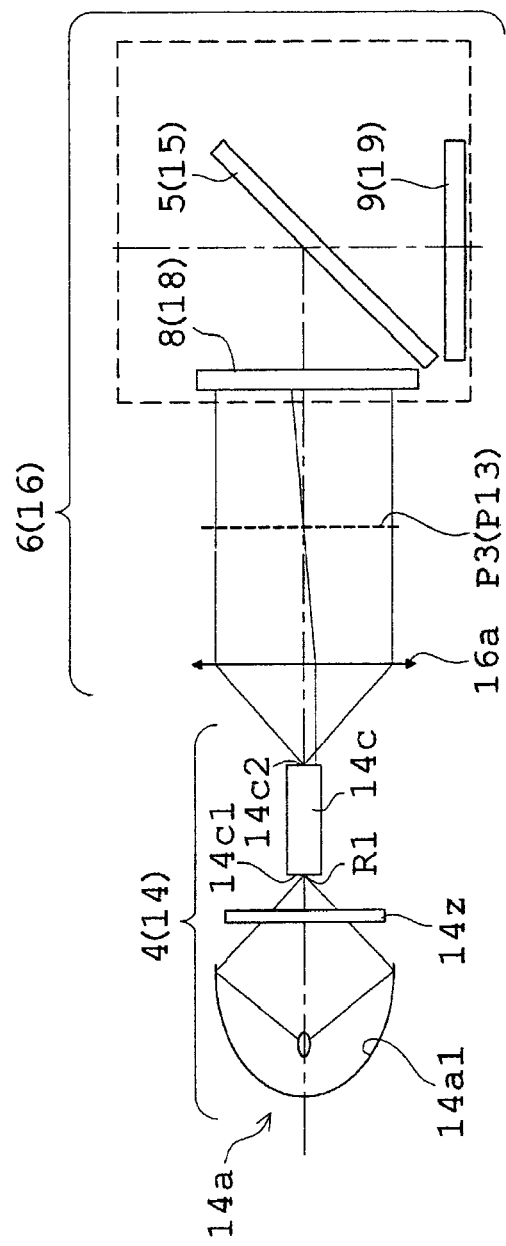
FIG. 12 is an explanatory view showing the arrangement of an illumination light source and a reflecting fluorescence illumination optical system in the microscope according to Embodiment 9 of the present invention.

FIG. 12 is an explanatory view showing the arrangement of an illumination light source and a reflecting fluorescence illumination optical system in the microscope according to Embodiment 9 of the present invention. In the microscope of Embodiment 9, the illumination light source 4 (14) has the collection-type reflector light source 14a and the integrator rod 14c. The reflecting fluorescence illumination optical system 6 (16) includes the collector lens 16a, the excitation filter 8 (18), and the dichroic mirror 5 (15). Also, in FIG. 12, reference numeral 9 (19) represents the barrier filter. The reflector light source 14a is constructed with the arc light source, such as a mercury lamp or a metal halide lamp, provided with the elliptical reflector mirror 14a1. The elliptical reflector mirror 14a1 is constructed so that a convergent beam is emitted by reflection to form the primary light source image at the primary imaging position R1. Also, instead of the collection-type reflector light source 14a, the parallel-beam-type reflector light source may be used so that a lens in which a parallel beam emitted from the parallel-beam-type reflector light source is condensed to perform the primary formation of the light source image of the reflector light source is interposed between the integrator rod 14c and the reflector light source. The illumination light source 4 (14) may be designed to use an LED or a short-arc extra-high voltage mercury lamp as another light source.

The integrator rod 14c is constructed with a columnar member of a square-column glass rod shape made from glass material with high ultraviolet transmittance or a light pipe including a hollow square-column mirror so that light incident on the interior repeats total reflection in turn and thereby is mixed and illumination distribution is equalized. The exit end face 14c2 of the integrator rod 14c serves as the plane of the secondary light source image. Also, the cross section of the integrator rod 14c is configured into a rectangular shape similar to the image pickup area of the image sensor (omitted from the figure). The integrator rod 14c is placed so that the entrance end face 14c1 is located at the primary imaging position R1 of the light source image of the reflector light source 14a.

The collector lens 16a is designed so that a divergent beam emerging from the exit end face 14c2 of the integrator rod 14c is converted into a parallel beam. The pupil position P3 (P13) conjugate with the pupil position of the objective lens (omitted from the figure) is situated between the collector lens 16a and the excitation filter 8 (18). The exit end face 14c2 is located at a position conjugate with the surface of the specimen (omitted from the figure). Whereby, the microscope of Embodiment 9 is such that light from the illumination light source traveling through the integrator rod 14c provides critical illumination for the surface of the specimen (omitted from the figure). Between the reflector light source 14a and the integrator rod 14c, the infrared cutoff filter 14z is interposed. Further, between the reflector light source 14a and the excitation filter 8 (18), the shutter section (omitted from the figure) for cutting off the light beam form the reflector light source 14a is provided.

The locations and structures of the objective lens (omitted from the figure), the imaging lens (omitted from the figure), the excitation filter 8 (18), the dichroic mirror 5 (15), the barrier filter 9 (19), the relay optical system (omitted from the figure), and other members are almost the same as in the microscope shown in FIG. 2 or the microscope of the first aspect shown in FIG. 3.

In the microscope of Embodiment 9 constructed as mentioned above, the convergent beam emitted from the reflector light source 14a forms the primary light source image at the primary imaging position R1 after the infrared wavelength is removed by the infrared cutoff filter 14z, and is incident on the entrance end face 14c1 of the integrator rod 14c. Light incident on the entrance end face 14c1 of the integrator rod 14c repeats reflection in the interior to thereby secure the equalization of intensity distribution of the light, and emerges as a divergent beam from the exit end face 14c2. The divergent beam emerging from the exit end face 14c2 of the integrator rod 14c is incident on the collector lens 16a. The divergent beam incident on the collector lens 16a is converted into a parallel beam by the collector lens 16a. The parallel beam converted by the collector lens 16a, as in the microscope shown in FIG. 2 or the microscope of the first aspect shown in FIG. 3, after traveling through the excitation filter 8 (18) and the dichroic mirror 5 (15), is relayed through the relay optical system (omitted from the figure) to form the image of the secondary light source by projecting the exit end face 14c2 of the integrator rod 14c on the surface of the specimen (omitted from the figure).

According to the microscope of Embodiment 9, the integrator rod 14c is provided in the reflecting fluorescence illumination optical system of the microscope in which the critical illumination is made, and hence light can be converted into the illumination beam of uniform planar light intensity distribution. Also, in general, when the integrator rod is used, unevenness of a light intensity due to angles of emergent rays is produced, but in the microscope of Embodiment 9, the unevenness of the light intensity is eliminated by using the means of the critical illumination and the light intensity can be equalized. Other functions and effects are almost the same as in the microscope shown in FIG. 2 or the microscope of the first aspect shown in FIG. 3.

Embodiment 10

Figure 13A:
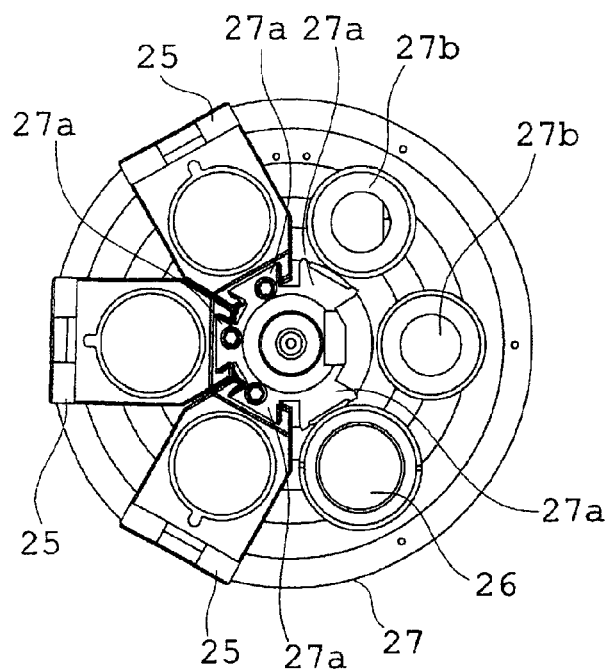
Figure 13B:
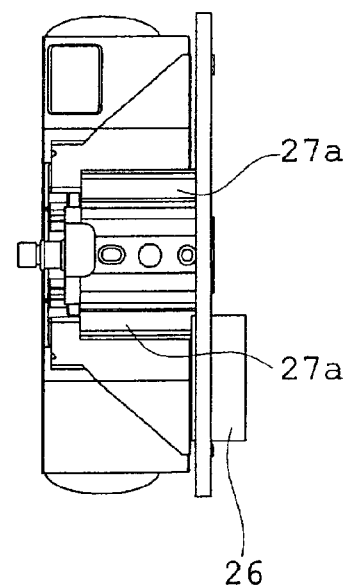
Figure 13C:
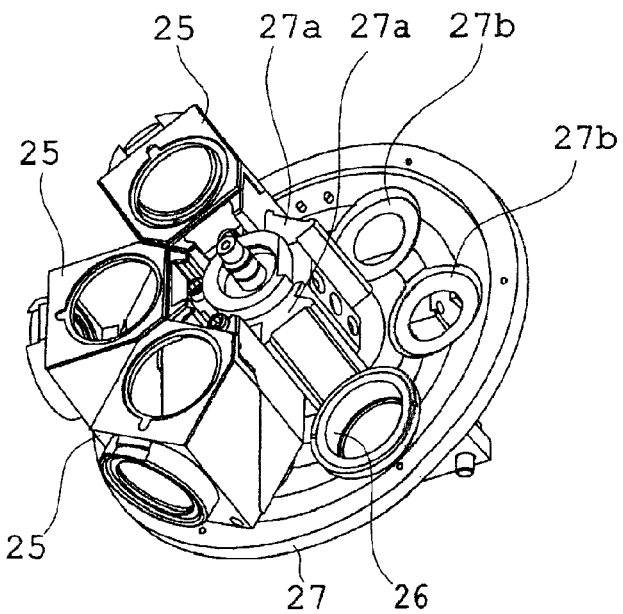

FIG. 13 is explanatory views showing an optical structure placed in the proximity of a pupil position conjugate with the pupil position of the objective lens in the microscope according to Embodiment 10 of the present invention, in which (a) is a plan view, looking from the objective lens side, (b) is a side view of (a), and (c) is a perspective view of (a), looking from the objective lens side. In the microscope of Embodiment 10, fluorescence cubes 25 and pupil modulation means 26 are provided in each of microscopes of Embodiments 1-9 shown in FIGS. 4-12 and are arranged on a turret 27 to be switchable with respect to an insertion and removal of each of the fluorescence cubes or the pupil modulation means in and out of the optical path between the relay optical system (omitted from the figure) and the imaging lens (omitted from the figure).

Each of the fluorescence cubes 25 has the dichroic mirror 5 (15), the barrier filter 9 (19), and the excitation filter 8 (18) (except for the arrangement of Embodiment 7), each of a different wavelength characteristic according to the observation application. Each fluorescence cube 25 is mounted to a fluorescence cube mounting portion 27a of the turret 27. A phase plate in which a phase film is zonally provided, a Nomarski prism (omitted from the figure), a Hofmann module (omitted from the figure), or a variable stop (omitted from the figure) is applicable to each of the pupil modulation means 26. In FIG. 13, an example where the phase plate is used is shown. Each pupil modulation means 26 is mounted to a pupil modulation means mounting portion 27b of the turret 27. The fluorescence cube 25 or the pupil modulation means 26, when inserted in the optical path between the relay optical system (omitted from the figure) and the imaging lens (omitted from the figure), is placed in the proximity of the position conjugate with the pupil position of the objective lens, formed between the relay optical system and the imaging lens. Also, the number of locations of the fluorescence cubes and the pupil modulation means on the turret 27 can be changed at will in accordance with the application.

Figure 14:
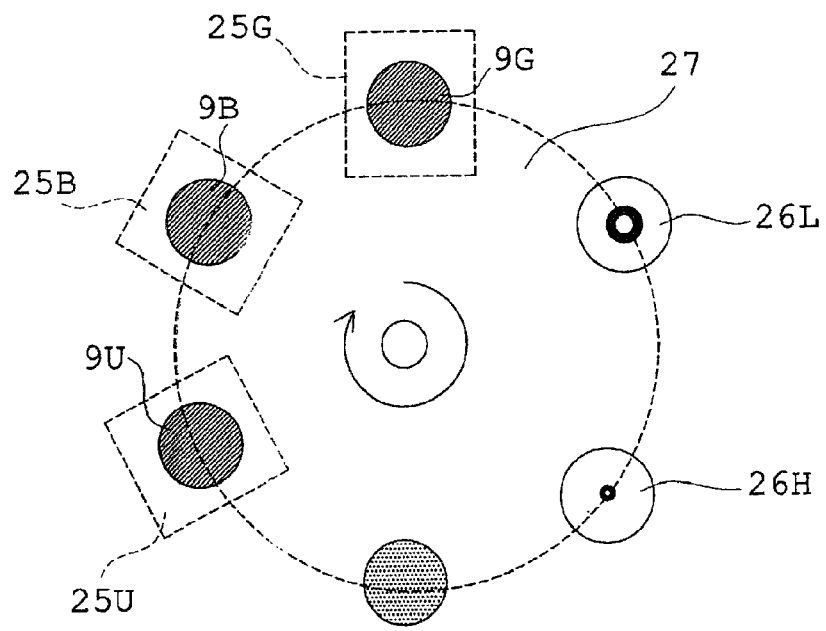
FIG. 14 is an explanatory view showing one example of an arrangement of fluorescence cubes and pupil modulation members in the microscope of Embodiment 10.

An example of the arrangement of the fluorescence cubes and the pupil modulation means in the microscope of Embodiment 10 is shown in FIG. 14. In the example of FIG. 14, on the turret 27, a fluorescence cube 25U having an ultraviolet light excitation filter (not shown), the dichroic mirror (not shown), and an ultraviolet light absorption filter 9U; a fluorescence cube 25B having a blue light excitation filter (not shown), the dichroic mirror (not shown), and a blue light absorption filter 9B; and a fluorescence cube 25G having a green light excitation filter (not shown), the dichroic mirror (not shown), and a green light absorption filter 9G are arranged as the fluorescence cubes 25, and a low-magnification phase plate 26L and a high-magnification phase plate 26H are arranged as the pupil modulation means 26.

Figure 15:
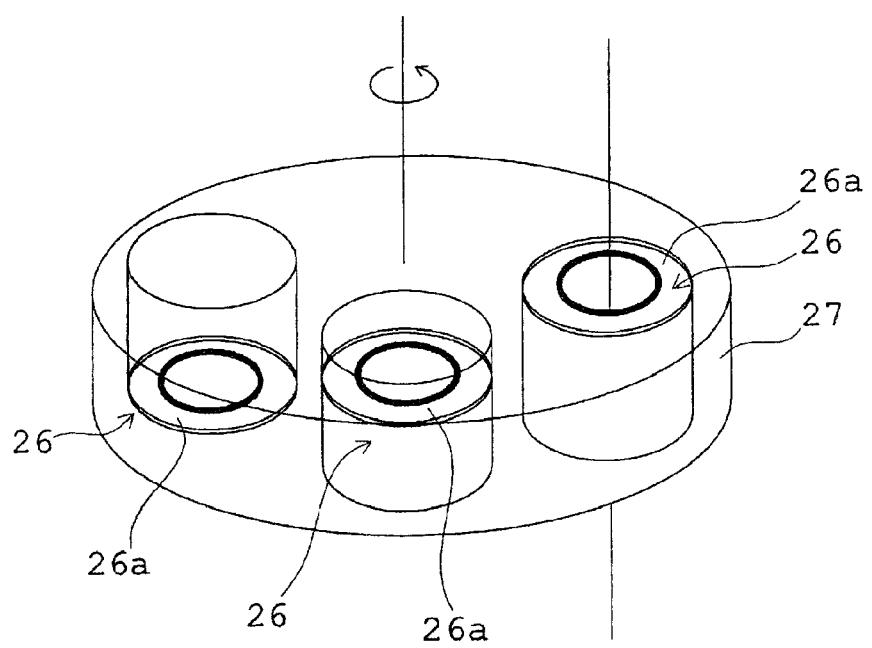
FIG. 15 is an explanatory view showing the positions of phase films where the phase films corresponding to objective lenses of different magnifications are mounted to a turret.

In the microscope of Embodiment 10, the phase plates as the pupil modulation means 26, as illustrated in FIG. 15, each have a phase film 26a at a different position in the direction of the optical axis so that each of the phase plates is located at the position conjugate with the pupil position of the objective lens (omitted from the figure), according to an objective lens (omitted from the figure) whose pupil position varies with the magnification, in a state where the phase plate is mounted on the turret 27. The locations and structures of the objective lens (omitted from the figure), the imaging lens (omitted from the figure), the excitation filter 8 (18), the dichroic mirror 5 (15), the barrier filter 9 (19), the relay optical system (omitted from the figure), and other members are almost the same as in the microscope shown in FIG. 2 or the microscope of the first aspect shown in FIG. 3.

In the microscope of Embodiment 10 constructed as mentioned above, when the turret 27 is turned and the fluorescence cube 25 is inserted in the optical path between the relay optical system (omitted from the figure) and the imaging lens (omitted from the figure), the fluorescence observation with reflecting illumination can be carried out. When the pupil modulation means 26 is inserted, observations, such as a phase contrast observation, a differential interference observation, and a Hofmann module contrast observation, with transmission illumination shown in FIG. 3 can be carried out. According to the microscope of the Embodiment 10, therefore, various microscope observations can be made by a simple switching operation. Other functions and effects are the same as in the microscopes of Embodiment 1-9 shown in FIGS. 4-12.

Figure 21B:
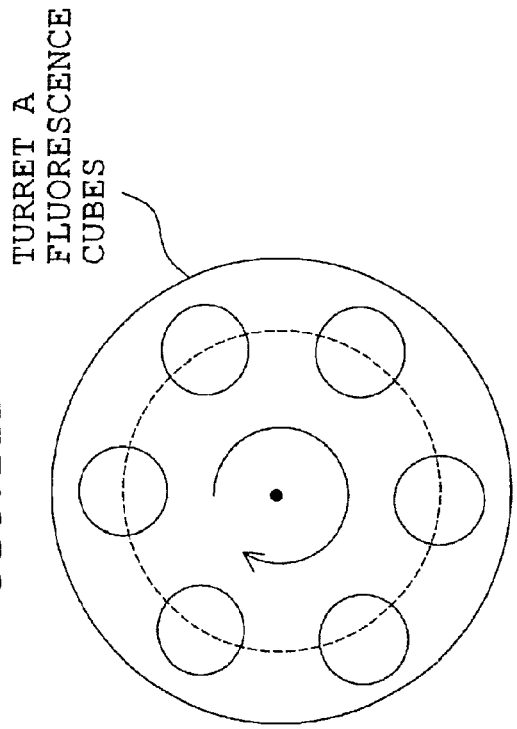
FIGS. 21A-21C are schematic diagrams that show the configuration in which fluorescence cubes and pupil modulation modules are held by different turrets, where
Figure 21C:
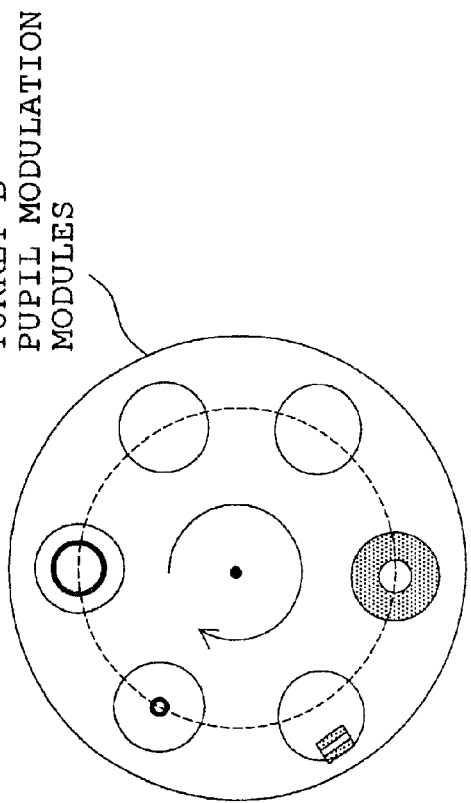
Figure 21A:
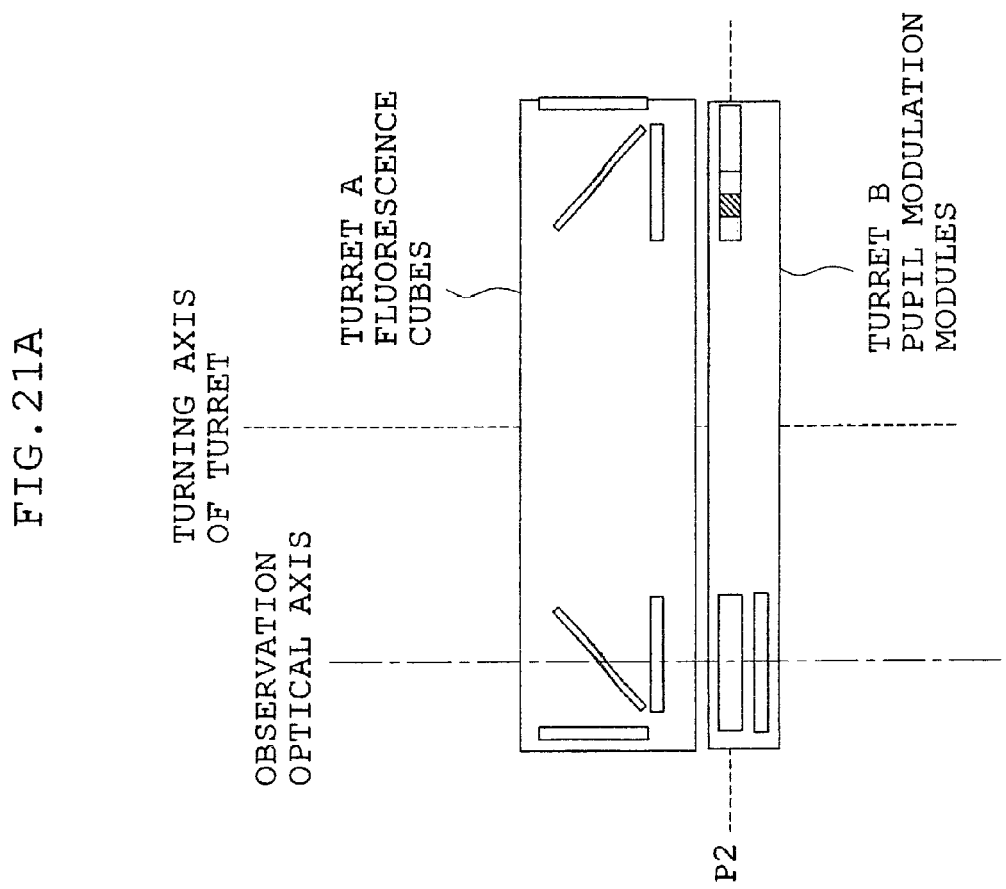

Also, in the example shown in FIG. 13, the fluorescence cubes and the pupil modulation means are arranged on the turret to be switchable with respect to the insertion and removal of either of them in and from the optical path, but even when a slider is used instead of the turret, the same effect is brought about. A turret having the fluorescence cubes and another turret having the pupil modulation means may be constructed as separate members so that a plurality of fluorescence cubes and a plurality of pupil modulation means are arranged on individual turrets. An example of such a configuration is shown in FIGS. 21A-21C. In this example, the fluorescence cubes are arranged in the turret A, while pupil modulation modules are arranged in the turret B. In such a structure, microscope observations in wider variety can be carried out by a simple operation.

Embodiment 11

The microscope of Embodiment 11 includes a plurality of objective lenses (omitted from the figure) of identical pupil positions, but of different magnifications, and a plurality of pupil modulation means (omitted from the figure), each having the phase film at an identical position in the direction of the optical axis. Other features are almost the same as in the microscope of Embodiment 10 shown in FIG. 13.

According to the microscope of Embodiment 11, since the position of each phase film is identical in the direction of the optical axis, there is no need to change the position of the phase film in accordance with the magnification of the objective lens and the design of the phase plate is facilitated. Moreover, since the pupil position of each objective lens is constant, regardless of the magnification, the pupil position in the illumination optical system becomes constant, and even when the magnification of the objective lens is changed, illumination can be made on the same condition. In addition, the fluorescence cube can be fixed in the proximity of the pupil position conjugate with the pupil of the objective lens, and hence the eclipse of the marginal light due to the fluorescence cub can be obviated even when the magnification of the objective lens is changed. Other functions and effects are almost the same as in the microscope of Embodiment 10.

INDUSTRIAL APPLICABILITY

The microscope of the present invention is useful in the fields of biology and medicine in which, for example, a lesion part is diagnosed with colors of cells imaged by carrying out the fluorescence observation, and it is required that various observation techniques, such as a light emission observation, a phase contrast observation, and a differential interference observation, are used and the observations of specimens are carried out with high accuracy.

The invention claimed is:

1. A microscope comprising:
an objective lens;
an imaging lens projecting light passing through the objective lens to form an image of a specimen;
an image sensor located at an imaging position where the image of the specimen is formed by the imaging lens;
an illumination light source;
a reflecting fluorescence illumination optical system including a fluorescence cube to illuminate the specimen with light, the fluorescence cube having at least a dichroic mirror that introduces light from the illumination light source into an optical path on an objective lens side and a barrier filter provided separately from the dichroic mirror in the fluorescence cube for cutting off unwanted light from the specimen; and
a relay optical system arranged between the objective lens and imaging lens, the relay optical system forming an intermediate image of the specimen at a position inside the relay optical system and relaying the intermediate image to the imaging lens,
wherein the fluorescence cube of the reflecting fluorescence illumination optical system is located between the relay optical system and a pupil conjugate position that is conjugate with a pupil position of the objective lens and that is formed between the relay optical system and the imaging lens, and
wherein the barrier filter is located at the pupil conjugate position.

2. The microscope according to claim 1, wherein a light beam from the specimen is nearly afocal at the pupil conjugate position.

3. The microscope according to claim 1, wherein the imaging lens is constructed with a zoom optical system or a variable magnification optical system whose magnification is changed stepwise.

4. The microscope according to any one of claims 1, 2 and 3, satisfying the following condition:

$$0.6 \leq |\beta| \leq 1.5$$

where $\beta$ is a pupil relay magnification of the relay optical system from the pupil position of the objective lens to the pupil conjugate position.

5. The microscope according to any one of claims 1, 2 and 3, satisfying the following condition:

$$\beta=1$$

where $\beta$ is a pupil relay magnification of the relay optical system.

6. The microscope according to claim 1, wherein a fly-eye lens is placed proximate to another pupil conjugate position that is conjugate with the pupil position of the objective lens and that is in the reflecting fluorescence illumination optical system.

7. The microscope according to claim 1, wherein the illumination light source is constructed with a reflector light source, an LED light source, or a fiber light source.

8. The microscope according to claim 1, having an integrator rod in the reflecting fluorescence illumination optical system.

9. The microscope according to claim 6, wherein
the illumination light source is constructed with a reflector light source;
the reflecting fluorescence illumination optical system has a beam conversion optical system carrying out a preset conversion with respect to a light beam emitted from the reflector light source to make a parallel beam emerge and the fly-eye lens; and
the fly-eye lens includes a first lens array whose entrance end faces are provided with a plurality of convex surfaces and a second lens array whose exit end faces are provided with a plurality of convex surfaces, integrally or separately constructed, so that the parallel beam emerging from the beam conversion optical system is split into a plurality of beams and a plurality of light source images of the reflector light source are formed proximate to the exit end faces of the second lens array.

10. The microscope according to claim 9, wherein
the reflector light source is constructed to make a convergent beam emerge therefrom so that a primary formation of a light source image is made, and
the beam conversion optical system is constructed with a collector lens that converts a light beam diverging from a position of the primary formation of the light source image into a parallel beam.

11. The microscope according to claim 9, wherein
the reflector light source is constructed to make a parallel beam emerge therefrom, and
the beam conversion optical system is constructed with an afocal system that converts the parallel beam emerging from the reflector light source into a parallel beam having a diameter nearly equal to a diameter of the fly-eye lens.

12. The microscope according to claim 11, wherein
the afocal system is constructed so that the parallel beam emerging from the reflector light source is condensed to make a primary formation of a light source image of the reflector light source inside the afocal system and then is converted into the parallel beam to emerge therefrom.

13. The microscope according to claim 6, wherein
the illumination light source has a reflector light source that emits a convergent beam to make a primary formation of a light source image and a filter having an entrance end face at a position of the primary formation of the light source image;
the reflecting fluorescence illumination optical system has a collector lens that converts a divergent beam emerging from an exit end face of the fiber into a parallel beam and the fly-eye lens; and the fly-eye lens includes a first lens array whose entrance end faces are provided with a plurality of convex surfaces and a second lens array whose exit end faces are provided with a plurality of convex surfaces, integrally or separately constructed, so that the parallel beam emerging from the collector lens is split into a plurality of beams and a plurality of light source images of the illumination light source are formed proximate to the exit end faces of the second lens array.

14. The microscope according to claim 6, wherein
the illumination light source has a reflector light source that emits a parallel beam, a lens that condenses the parallel beam emitted from the reflector light source to make a primary formation of a light source image of the reflector light source, and a fiber having an entrance end face at a position of the primary formation of the light source image;
the reflecting fluorescence illumination optical system has a collector lens that converts a divergent beam emerging from an exit end face of the fiber into a parallel beam and the fly-eye lens; and
the fly-eye lens has a first lens array whose entrance end faces are provided with a plurality of convex surfaces and a second lens array whose exit end faces are provided with a plurality of convex surfaces, integrally or separately constructed, so that the parallel beam emerging from the collector lens is split into a plurality of beams and a plurality of light source images of the reflector light source are formed proximate to the exit end faces of the second lens array.

15. The microscope according to claim 6, wherein
the illumination light source has a reflector light source that emits a convergent beam to make a primary formation of a light source image of the reflector light source and an integrator rod that has an entrance end face at a position of the primary formation of the light source image;
the reflecting fluorescence illumination optical system has a collector lens that converts a divergent beam emerging from an exit end face of the integrator rod into a parallel beam and the fly-eye lens; and
the fly-eye lens includes a first lens array whose entrance end faces are provided with a plurality of convex surfaces and a second lens array whose exit end faces are provided with a plurality of convex surfaces, integrally or separately constructed, so that the parallel beam emerging from the collector lens is split into a plurality of beams and a plurality of light source images of the reflector light source are formed proximate to the exit end faces of the second lens array.

16. The microscope according to claim 6, wherein
the illumination light source has a reflector light source that emits a parallel beam, a lens that condenses the parallel beam emitted from the reflector light source to make a primary formation of a light source image of the reflector light source, and an integrator rod having an entrance end face at a position of the primary formation of the light source image;
the reflecting fluorescence illumination optical system has a collector lens that converts a divergent beam emerging from an exit end face of the integrator rod into a parallel beam and the fly-eye lens; and
the fly-eye lens has a first lens array whose entrance end faces are provided with a plurality of convex surfaces and a second lens array whose exit end faces are provided with a plurality of convex surfaces, integrally or separately constructed, so that the parallel beam emerging from the collector lens is split into a plurality of beams and a plurality of light source images of the reflector light source are formed proximate to the exit end faces of the second lens array.

17. The microscope according to claim 6, wherein
the illumination light source is constructed with an LED light source;
the reflecting fluorescence illumination optical system has a collector lens that converts a divergent beam emitted from the LED light source into a parallel beam to emerge, and the fly-eye lens; and
the fly-eye lens has a first lens array whose entrance end faces are provided with a plurality of convex surfaces and a second lens array whose exit end faces are provided with a plurality of convex surfaces, integrally or separately constructed, so that the parallel beam emerging from the collector lens is split into a plurality of beams and a plurality of light source images of the LED light source are formed proximate to the exit end faces of the second lens array.

18. The microscope according to claim 6, wherein
the illumination light source has a plurality of LED light sources of different wavelengths, a plurality of first collector lenses provided opposite to the plurality of LED light sources, to convert divergent beams emitted form the LED light sources into parallel beams, path combining means that combine optical paths of the parallel beams emerging from the first collector lenses, a light-condensing optical system that condenses a parallel beam combined through the path combining means to make a primary formation of a light source image of each of the LED light sources, and a fiber having an entrance end face at a position of the primary formation of the light source image;
the reflecting fluorescence illumination optical system has a second collector lens that converts a divergent beam emerging from an exit end face of the fiber into a parallel beam to emerge, and the fly-eye lens; and
the fly-eye lens has a first lens array whose entrance end faces are provided with a plurality of convex surfaces and a second lens array whose exit end faces are provided with a plurality of convex surfaces, integrally or separately constructed, so that the parallel beam emerging from the second collector lens is split into a plurality of beams and a plurality of light source images of the illumination light source are formed proximate to the exit end faces of the second lens array.

19. The microscope according to claim 6, wherein
the illumination light source has a plurality of LED light sources of different wavelengths, a reflector light source that emits a convergent beam to make a primary formation of a light source image of the reflector light source, and a fiber having an entrance end face at a position of the primary formation of the light source image of the reflector light source;
the reflecting fluorescence illumination optical system has a plurality of LED emitted-beam conversion collector lenses provided opposite to the plurality of LED light sources, to convert divergent beams emitted from the LED light sources into parallel beams to emerge, path combining means that combine optical paths of the parallel beams emerging from the LED emitted-beam conversion collector lenses, a fiber emergent-beam conversion collector lens that converts a divergent beam emerging from an exit end face of the fiber into a parallel beam to emerge, a mirror placed to be movable in and out of an optical path of the path combining means so that the parallel beam emerging from the fiber emergent-beam conversion collector lens is incident on the fly-eye lens when the mirror is inserted in the optical path, and the fly-eye lens; and the fly-eye lens has a first lens array whose entrance end faces are provided with a plurality of convex surfaces and a second lens array whose exit end faces are provided with a plurality of convex surfaces, integrally or separately constructed, so that the parallel beam emerging from each of the LED emitted-beam conversion collector lenses or from the fiber emergent-beam conversion collector lens is split into a plurality of beams and a plurality of light source images of the illumination light source are formed proximate to the exit end faces of the second lens array.

20. The microscope according to claim 6, wherein the illumination light source has a plurality of LED light sources of different wavelengths, a reflector light source that emits parallel beam, a lens that condenses the parallel beam emitted from the reflector light source to make a primary formation of a light source image of the reflector light source, and a fiber having an entrance end face at a position of the primary formation of the light source image of the reflector light source;

the reflecting fluorescence illumination optical system has a plurality of LED emitted-beam conversion collector lenses provided opposite to the plurality of LED light sources, converting divergent beams emitted from the LED light sources into parallel beams to emerge, path combining means that combine optical paths of the parallel beams emerging from the LED emitted-beam conversion collector lenses, a fiber emergent-beam conversion collector lens that converts a divergent beam emerging from an exit end face of the fiber into a parallel beam to emerge, a mirror placed to be movable in and out of an optical path of the path combining means so that the parallel beam emerging from the fiber emergent-beam conversion collector lens is incident on the fly-eye lens when the mirror is inserted in the optical path, and the fly-eye lens; and the fly-eye lens has a first lens array whose entrance end faces are provided with a plurality of convex surfaces and a second lens array whose exit end faces are provided with a plurality of convex surfaces, integrally or separately constructed, so that the parallel beam emerging from each of the LED emitted-beam conversion collector lenses or from the fiber emergent-beam conversion collector lens is split into a plurality of beams and a plurality of light source images of the illumination light source are formed proximate to the exit end faces of the second lens array.

21. The microscope according to claim 1, wherein the illumination light source has a reflector light source that emits a convergent beam to make a primary formation of a light source image of the reflector light source and an integrator rod having an entrance end face at a position of the primary formation of the light source image of the reflector light source, and the reflecting fluorescence illumination optical system has a collector lens that converts a divergent beam emerging from an exit end face of the integrator rod into a parallel beam.

22. The microscope according to claim 1, wherein the illumination light source has a reflector light source that emits a parallel beam, a lens that condenses the parallel beam emitted from the reflector light source to make a primary formation of a light source image of the reflector light source, and an integrator rod having an entrance end face at a position of the primary formation of the light source image, and the reflecting fluorescence illumination optical system has a collector lens that converts a divergent beam emerging from an exit end face of the integrator rod into a parallel beam.

23. The microscope according to claim 1, wherein the illumination light source has an LED light source, a lens that condenses a divergent beam emitted from the LED light source to make a primary formation of a light source image of the LED light source, and an integrator rod having an entrance end face at a position of the primary formation of the light source image, and the reflecting fluorescence illumination optical system has a collector lens that converts a divergent beam emerging from an exit end face of the integrator rod into a parallel beam.

24. The microscope according to claim 1, wherein the objective lens, the imaging lens, and the relay optical system are constructed to be nearly telecentric optical systems on a surface of an object, at a position of the intermediate image, and on a surface of the image sensor, respectively.

25. The microscope according to claim 1, wherein an excitation filter is provided in the fluorescence cube.

26. The microscope according to claim 1, further comprising a pupil modulator configured to be locatable proximate to the pupil conjugate position.

27. The microscope according to claim 26, wherein the pupil modulator is a variable stop.

28. The microscope according to claim 26, wherein the pupil modulator is constructed with a member in which a phase film is zonally provided, and the microscope further comprises a transmitting illumination system constructed and arranged to perform irradiation with zonal illumination light corresponding to the member in which the phase film is zonally provided.

29. The microscope according to claim 26, wherein the pupil modulator is a Nomarski prism.

30. The microscope according to claim 26, wherein the pupil modulator is a Hofmann module.

31. The microscope according to claim 26, wherein the pupil modulator is constructed to be movable in and out of the optical path.

32. The microscope according to claim 31, further comprising:

a turret on which the fluorescence cube and the pupil modulator are arranged, switchable with respect to an insertion and removal of the fluorescence cube or the pupil modulator in and out of an optical path between the relay optical system and the imaging lens so that the fluorescence cube or the pupil modulator, when inserted in the optical path between the relay optical system and the imaging lens, is placed proximate to the pupil conjugate position.

33. The microscope according to claim 31, further comprising:

a slider on which the fluorescence cube and the pupil modulator are arranged, switchable with respect to an insertion and removal of the fluorescence cube or the pupil modulator in and out of an optical path between the relay optical system and the imaging lens so that the fluorescence cube or the pupil modulator, when inserted in the optical path between the relay optical system and the imaging lens, is placed proximate to the pupil conjugate position.

34. The microscope according to claim 31, further comprising:
- at least one other fluorescence cube having at least a dichroic mirror and a barrier filter so that the microscope has, in total, a plurality of fluorescence cubes, each of which has at least a dichroic mirror and a barrier filter for cutting off unwanted light, out of light from the specimen;
- at least one another pupil modulator so that the microscope has, in total, a plurality of pupil modulators;
- a first turret on which the plurality of fluorescence cubes are arranged, switchable with respect to an insertion and removal of each of the plurality of fluorescence cubes in and out of an optical path between the relay optical system and the imaging lens; and
- a second turret on which the plurality of pupil modulators are arranged, switchable with respect to an insertion and removal of each of the plurality of pupil modulators in and out of the optical path between the relay optical system and the imaging lens,
- wherein any one of the fluorescence cubes or any one of the pupil modulators, when inserted in the optical path between the relay optical system and the imaging lens, is arranged proximate to the pupil conjugate position.

35. The microscope according to claim 31, further comprising:
- at least one other fluorescence cube having at least a dichroic mirror and a barrier filter so that the microscope has, in total, a plurality of fluorescence cubes, each of which has at least a dichroic mirror and a barrier filter for cutting off unwanted light, out of light from the specimen;
- at least one other pupil modulator so that the microscope has, in total, a plurality of pupil modulators;
- a first slider on which the plurality of fluorescence cubes are arranged, switchable with respect to an insertion and removal of each of the plurality of fluorescence cubes in and out of an optical path between the relay optical system and the imaging lens; and
- a second slider on which the plurality of pupil modulators are arranged, switchable with respect to an insertion and removal of each of the plurality of pupil modulators in and out of the optical path between the relay optical system and the imaging lens,
- wherein any one of the fluorescence cubes or any one of the pupil modulators, when inserted in the optical path between the relay optical system and the imaging lens, is arranged proximate to the pupil conjugate position.

36. The microscope according to claim 31, comprising a plurality of pupil modulators, each of which has a phase film at a different position in a direction of an optical axis, in accordance with a plurality of objective lenses having different pupil positions.

37. The microscope according to claim 31, comprising a plurality of objective lenses of identical pupil positions, but of different magnifications, and a plurality of pupil modulators, each of which has a phase film at an identical position in a direction of an optical axis.

38. The microscope according to claim 1, wherein an image restriction member for partially blocking illumination light from the reflecting fluorescence illumination optical system is constructed to be locatable proximate to an imaging position where an intermediate image of the specimen is formed through the relay optical system.

39. The microscope according to claim 38, wherein the image restriction member is a rotatable Nipkow disk.

40. The microscope according to claim 38, wherein the image restriction member is a rotatable slit member.

41. The microscope according to claim 38, wherein the image restriction member is constructed so that an aperture thereof, through which illumination light from the reflecting fluorescence illumination optical system passes, is configured into a rectangular shape corresponding to a shape of an image pickup surface of the image sensor.

42. The microscope according to claim 1, wherein a path deflecting member is located at a preset place between the objective lens and the relay optical system for deflecting an optical path toward the imaging lens in a nearly horizontal direction.

43. The microscope according to claim 42, wherein a path splitting member is provided at a preset position in the optical path toward the imaging lens as deflected by the path deflecting member, for splitting the optical path into an optical path to be picked up by the image sensor and an optical path for visual observation.

44. The microscope according to claim 1, wherein an autofocus correction mechanism is provided between the objective lens and the imaging lens.

* * * * *